(12) United States Patent
Oikawa et al.

(10) Patent No.: US 9,364,152 B2
(45) Date of Patent: Jun. 14, 2016

(54) OBJECT INFORMATION ACQUIRING APPARATUS

(75) Inventors: Katsuya Oikawa, Tokyo (JP); Haruo Yoda, Nishitama-gun (JP)

(73) Assignee: CANON KABUSHIKI KAISHA, Tokyo (JP)

( * ) Notice: Subject to any disclaimer, the term of this patent is extended or adjusted under 35 U.S.C. 154(b) by 0 days.

(21) Appl. No.: 13/982,795

(22) PCT Filed: Jan. 31, 2012

(86) PCT No.: PCT/JP2012/000627
§ 371 (c)(1),
(2), (4) Date: Jul. 31, 2013

(87) PCT Pub. No.: WO2012/108143
PCT Pub. Date: Aug. 16, 2012

(65) Prior Publication Data
US 2013/0308850 A1 Nov. 21, 2013

(30) Foreign Application Priority Data

Feb. 9, 2011 (JP) .................................. 2011-026095

(51) Int. Cl.
*A61B 5/00* (2006.01)
*G01S 15/89* (2006.01)
*A61B 5/06* (2006.01)
*G01S 7/52* (2006.01)
(Continued)

(52) U.S. Cl.
CPC .............. *A61B 5/0033* (2013.01); *A61B 5/066* (2013.01); *G01S 7/52085* (2013.01);
(Continued)

(58) Field of Classification Search
CPC .... A61B 5/0033; A61B 5/066; A61B 8/4477; A61B 8/483; A61B 2019/5276; G01S 15/8945; G01S 15/8927; G01S 15/8993; G01S 15/8997; G01S 7/52085; G01S 15/8918
See application file for complete search history.

(56) References Cited

U.S. PATENT DOCUMENTS 4,726,230 A * 2/1988 Yoshikawa et al. ............. 73/607
5,549,111 A * 8/1996 Wright et al. ................. 600/443
(Continued)

FOREIGN PATENT DOCUMENTS

| JP | S58-141139 | 8/1983 |
|---|---|---|
| JP | 2009-028366 | 2/2009 |
| WO | WO 2010137451 A2 * | 12/2010 |

OTHER PUBLICATIONS

JPO Office Action issued on Nov. 28, 2014 in counterpart Japanese patent application 2011-026095, with translation.

*Primary Examiner* — Manav Seth
(74) *Attorney, Agent, or Firm* — Fitzpatrick, Cella, Harper & Scinto

(57) ABSTRACT

There is used an object information acquiring apparatus including a probe for electrically scanning an object in first direction and mechanically scanning in second direction intersecting with the first direction, a first delay-and-sum unit for operating a delay-and-sum on a received signal, a memory for storing a first delay-and-sum signal for each plane in the second direction, a selecting unit for selecting signals corresponding to M sectional planes from among the stored signals, a second delay-and-sum unit for operating a delay-and-sum on the selected signals in the second direction, and a unit for acquiring image in the object from the second delay-and-sum signal, the second delay-and-sum unit switching, according to the mechanical scanning, a first case in which M signals are fixed and a delay pattern is varied and a second case in which a set of the M signals is varied and the delay pattern is fixed.

8 Claims, 10 Drawing Sheets

(51) Int. Cl.
*A61B 8/00* (2006.01)
*A61B 8/08* (2006.01)

(52) U.S. Cl.
CPC ........ G01S 15/8927 (2013.01); G01S 15/8945 (2013.01); G01S 15/8993 (2013.01); G01S 15/8997 (2013.01); *A61B 8/4477* (2013.01); *A61B 8/483* (2013.01); *G01S 15/8918* (2013.01)

(56) References Cited

U.S. PATENT DOCUMENTS

| | | | |
|---|---|---|---|
| 6,013,032 A * | 1/2000 | Savord | 600/443 |
| RE36,564 E * | 2/2000 | Schwartz et al. | 600/447 |
| 6,106,471 A * | 8/2000 | Wiesauer et al. | 600/443 |
| 6,292,433 B1 * | 9/2001 | Gilbert et al. | 367/138 |
| 6,671,227 B2 * | 12/2003 | Gilbert et al. | 367/138 |
| 7,593,449 B2 * | 9/2009 | Shattil | 375/130 |
| 8,241,218 B2 | 8/2012 | Hirama | 600/459 |
| 2009/0043209 A1 * | 2/2009 | Hirama | 600/459 |
| 2009/0275837 A1 | 11/2009 | Shiina et al. | 600/459 |
| 2009/0299185 A1 | 12/2009 | Oikawa et al. | 600/447 |
| 2011/0128816 A1 | 6/2011 | Baba et al. | 367/11 |
| 2012/0044785 A1 | 2/2012 | Yoda et al. | 367/92 |
| 2012/0281902 A1 | 11/2012 | Oikawa et al. | 382/131 |
| 2012/0314534 A1 | 12/2012 | Yoda et al. | 367/7 |

* cited by examiner

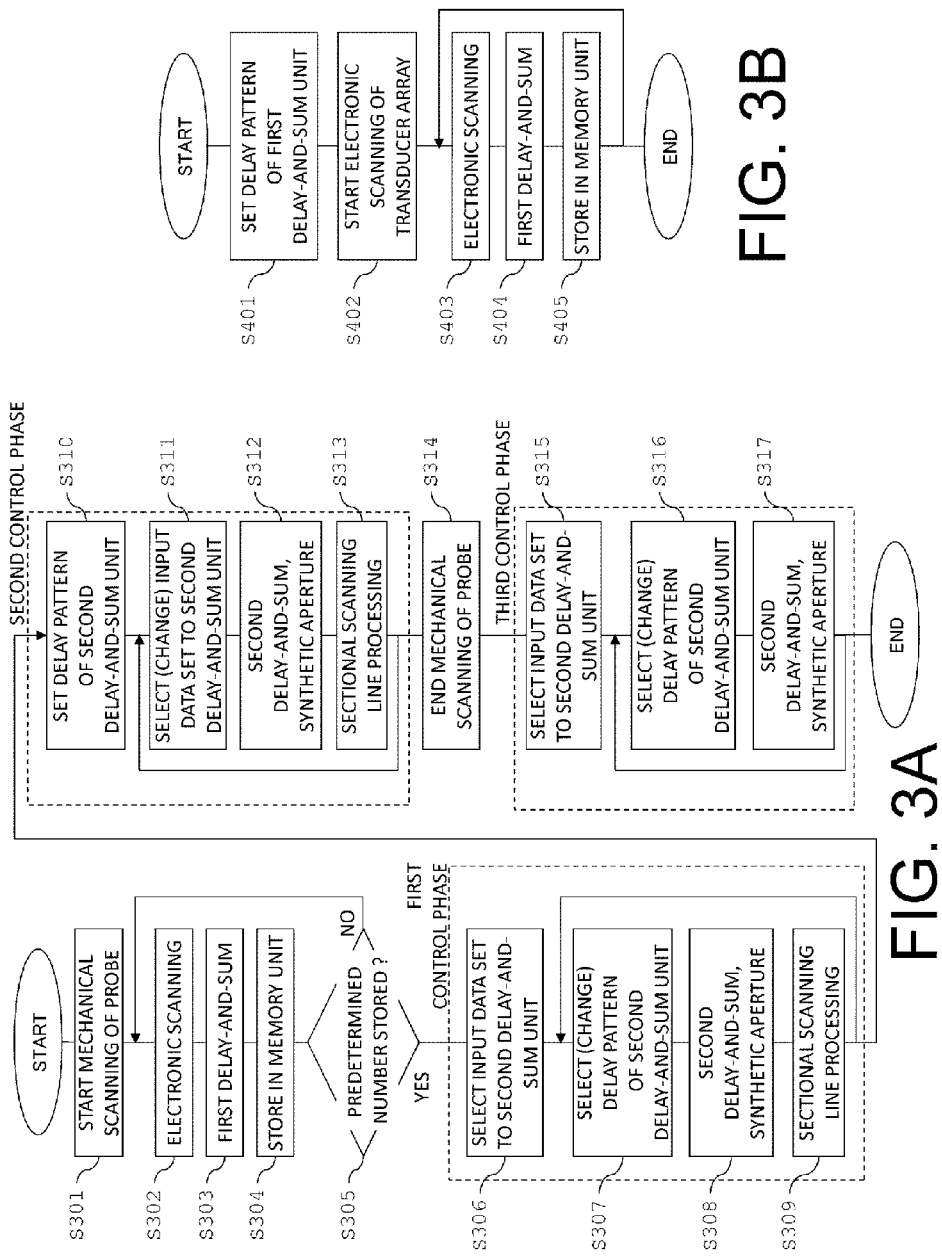

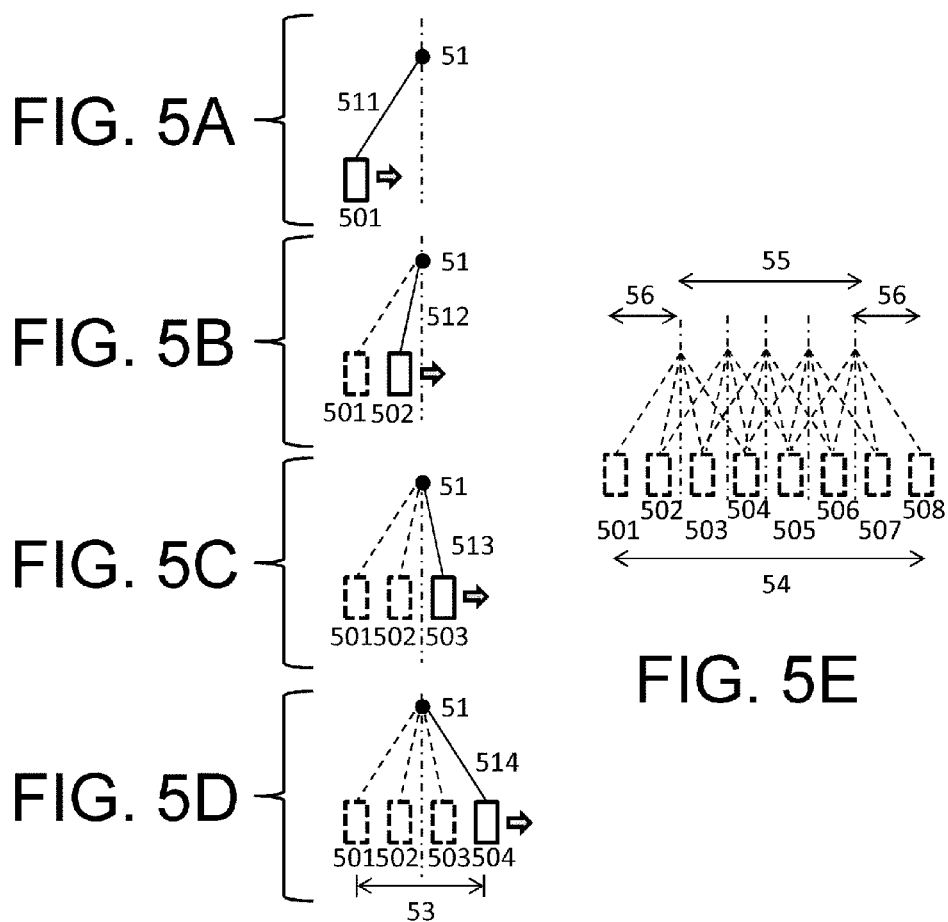

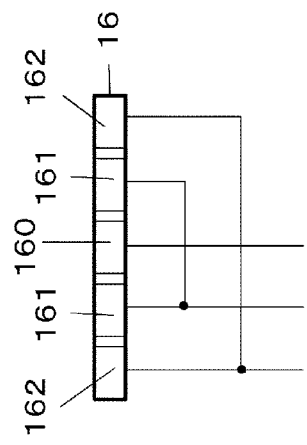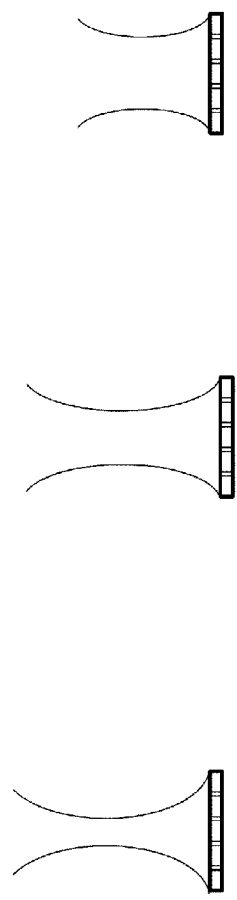

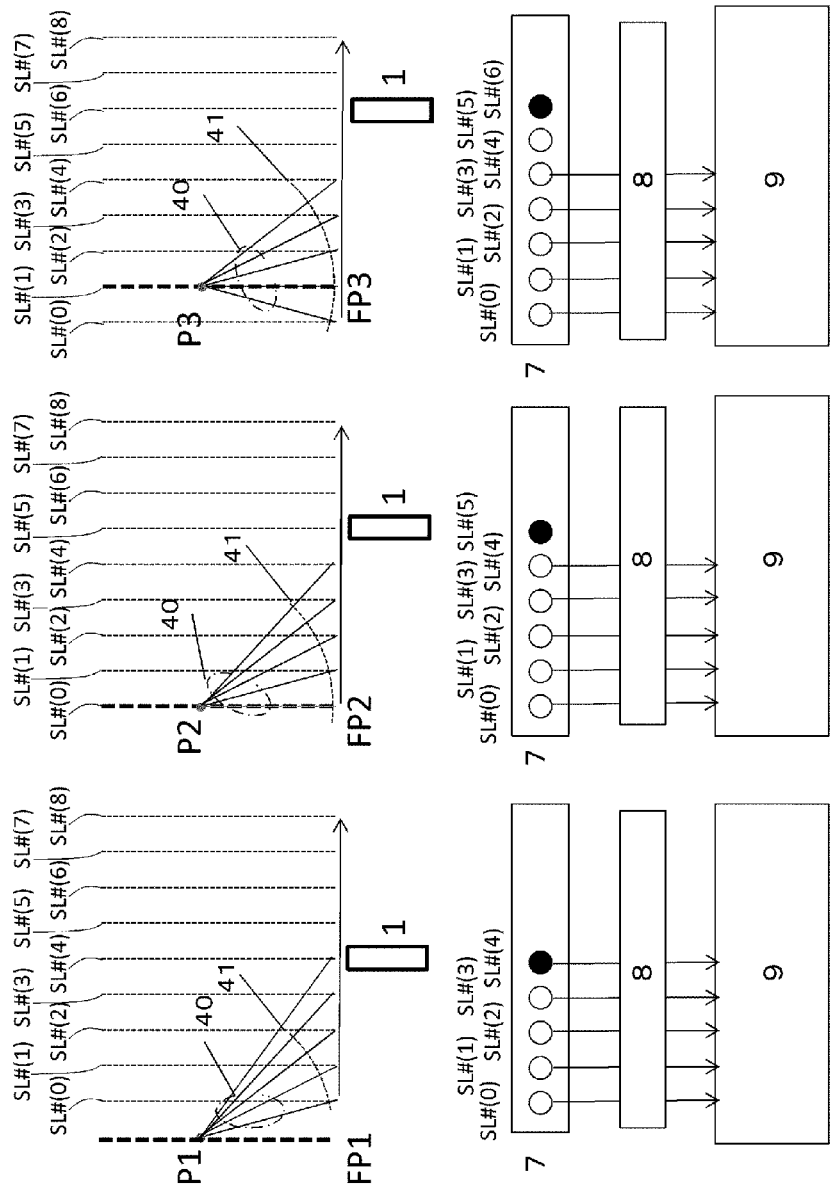

OBJECT INFORMATION ACQUIRING APPARATUS

TECHNICAL FIELD

The present invention relates to an object information acquiring apparatus for carrying out a synthetic aperture.

BACKGROUND ART

As a powerful diagnostic imaging apparatus for early detecting a breast cancer, conventionally, an X ray mammography apparatus is widely known. On the other hand, a method of acquiring a wide range of three-dimensional image data by using a low invasive ultrasound echo in place of X rays accompanied by an exposure is disclosed in PTL1 (Patent Literature 1) or the like, for example. The PTL1 discloses an apparatus for acquiring a three-dimensional ultrasound echo image by carrying out electronic scanning while mechanically moving an ultrasound probe (which will be hereinafter also referred to as a probe).

As a method of acquiring a three-dimensional ultrasound echo image, there is well known a method of carrying out three-dimensional electronic scanning by using a two-dimensional transducer array in which elements are arranged two-dimensionally. In order to carry out the three-dimensional electronic scanning over a wide range of imaging region with a high resolution, however, there are problems in that the number of the elements in the two-dimensional transducer array is increased, a processing scale is increased with the increase in the number of the elements, a scanning time is prolonged, and the like. For this reason, it is hard to constitute a practical ultrasound diagnostic imaging apparatus. On the other hand, since an apparatus in which mechanical scanning and electronic scanning of a probe are combined can easily pick up an image of a wide range of regions in an object, it can have a suitable structure as a three-dimensional image acquiring apparatus of an imaging region within a wide range such as an ultrasound mammography.

CITATION LIST

Patent Literature

[PTL 1]
Japanese Patent Application Publication No. 2009-028366

SUMMARY OF INVENTION

Technical Problem

In order to mechanically move a probe, thereby acquiring a three-dimensional echo image in a wide region, there is a method of acquiring an echo image while continuously moving a probe to be electronically scanned in a one-dimensional direction in an orthogonal direction to the electronic scanning direction (which will be hereinafter referred to as an elevation direction). The method is the most advantageous on a speed and cost basis. In this case, it is possible to reconstitute a single tomographic slice image through the electronic scanning of an ultrasound beam. Therefore, it is possible to acquire a three-dimensional image of a whole mechanical scanning region by stacking the tomographic slice image created in each position in the elevation direction.

However, this method has a problem in that an image resolution in the elevation direction is considerably reduced as compared with an image resolution in a slice surface. As a first reason, a physical burden of an object is increased with a delay of the mechanical scanning of the probe to reduce an acquisition pitch of the tomographic slice surface. Therefore, the mechanical scanning is to be quickened to some degree, thereby causing a pixel density in the elevation direction to be low. In a one-dimensional array probe in which the electronic scanning is carried out by using a one-dimensional transducer array, furthermore, there is also a problem in that an effective aperture angle in the elevation direction is smaller than that in an electronic scanning direction and a reconstitution resolution in the elevation direction is thus deteriorated.

The PTL1 discloses an apparatus for interpolating data acquired through electronic scanning in different positions in the elevation direction in accordance with the mechanical scanning of a probe. In other words, there is disclosed an apparatus for carrying out an interpolation between tomographic slice surfaces. Consequently, it is possible to suppress a reduction in a pixel density in the elevation direction. Furthermore, there is disclosed an apparatus for carrying out a processing utilizing a synthetic aperture principle by using data acquired in a plurality of different positions in an elevation direction, thereby inhibiting a resolution from being reduced due to an effective aperture angle in the elevation direction.

A method of inhibiting the resolution from being reduced due to the effective aperture angle in the elevation direction by using the synthetic aperture principle will be described with reference to FIGS. 5A to 5D. In FIGS. 5A to 5D, the reference numerals 501 to 504 denote a position of a probe. FIG. 5 is a projection view showing a surface constituted by the elevation direction and a depth direction of the object, in which a plurality of elements is arranged in an inner direction of the paper. In other words, the inner direction of the paper indicates an electronic scanning direction. The probe gathers an ultrasound received beam signal through electronic scanning over a tomographic slice surface while carrying out mechanical scanning in order of 501 to 504 in the elevation direction. The reference numeral 51 denotes a center of a target region for executing a delay-and-sum by using the synthetic aperture method, that is, a focal point. The reference numerals 511 to 514 denote a propagation path for an ultrasound echo from the probe to the focal point 51 in the probe positions 501 to 504, respectively. The probe acquires an ultrasound echo signal in each of the positions (501, 502, . . . ) moved depending on the mechanical scanning. Then, the ultrasound echo signal is stored and there is carried out the delay-and-sum for giving a delay to each acquired ultrasound echo signal to add the signal in order to offset propagation times of the propagation paths 511 to 514 in the respective positions. Consequently, it is possible to create an ultrasound received beam signal focused on the focal point 51.

The above operation can be combined with the electronic scanning to be carried out in each elevation position. In other words, referring to transmitted/received ultrasound beam scanning over the tomographic slice surface which is to be carried out by the electronic scanning, a transmitted/received beam is formed in the tomographic slice surface and a delay-and-sum signal (an ultrasound received beam signal) obtained by executing a normal delay-and-sum on a received signal is stored. Next, referring to a delay-and-sum signal of an ultrasound received beam signal corresponding to each tomographic slice surface which is generated depending on the probe mechanical scanning, the delay-and-sum in the elevation direction is carried out.

At this time, there is required a waveform memory for storing delay-and-sum signals acquired and created in the respective positions depending on the mechanical scanning of the probe. As a method, it is also possible to once store all of signals acquired in the mechanical scanning in the waveform memory and to then carry out the delay-and-sum in the elevation direction after the mechanical scanning. In that case, however, a real time property of an image reconfiguration processing is lost, and furthermore, a large capacity waveform memory is required. For this reason, it is preferable to employ a structure in which the delay-and-sum in the elevation direction is successively carried out (in a real time if possible) depending on the mechanical scanning of the probe.

FIG. 5E is a typical view showing the case in which a delay-and-sum for a synthetic aperture in the elevation direction is carried out by using delay-and-sum signals taken by the electronic scanning in four of eight probe positions (501 to 508) through the mechanical scanning of the probe. In order to form single synthetic imaging surface data through the synthetic aperture by using the signals in the four probe positions, it is sufficient to store, in the waveform memory, signals corresponding to at least tomographic slice surfaces (four slice surfaces in this example). In other words, the delay-and-sum in the elevation direction is started when the probe position reaches 504. With the movement of the probe position from 505 to 508, then, the delay-and-sum in the elevation direction is carried out and a result is output, and at the same time, the acquired signal is stored in the waveform memory. At this time, it is possible to effectively use the capacity of the waveform memory by storing a newly acquired signal in an overwriting form in the waveform memory or discarding an unnecessary signal. Moreover, the real time property of the image reconfiguration processing is also ensured in order to sequentially obtain the synthetic imaging surface data based on the delay-and-sum in the elevation direction in accordance with the mechanical scanning of the probe.

Referring to the delay-and-sum in the elevation direction using the synthetic aperture principle, a width (53 in FIG. 5D) of the probe position in the elevation direction in which the delay-and-sum is carried out corresponds to an aperture width obtained by a plurality of transducer elements in normal electronic scanning. Furthermore, an interval (a pitch) between the respective probe positions corresponds to a pitch between the transducer elements. By setting these values to be equal to an element pitch of a transducer array of a probe or an aperture width of electronic scanning, it is also possible to obtain an equivalent resolution to a B mode image in a tomographic slice surface in the elevation direction.

In the case in which the delay-and-sum in the elevation direction is successively carried out depending on the mechanical scanning of the probe, however, the following problem is caused.

In FIG. 5E, a single tomographic slice surface is constituted by carrying out the delay-and-sum in the elevation direction in a predetermined (fixed) delay pattern by using the signals in the four probe positions. For this reason, an elevation region 55 capable of carrying out a 3D image construction is reduced with respect to a probe scanning range 54. Therefore, a dead zone 56 to be a region in which the 3D image construction cannot be carried out is generated in the vicinity of the start and end of the probe scanning. In other words, an imaging range is smaller than a mechanical scanning range. A width of the dead zone is increased when the number of the probe positions in the elevation direction to be used in the synthetic aperture or a pitch thereof is increased. On the other hand, it is necessary to decrease the number of the probe positions or the pitch thereof in order to reduce a dead zone width. Consequently, an elevation resolution is reduced. For this reason, it is necessary to take a wider range in which the probe is subjected to the mechanical scanning as compared with a necessary acquiring region. As a result, an apparatus scale or structure is increased or a scanning time is prolonged. In the case of an application to a diagnostic apparatus such as a mammography apparatus, particularly, an excessive burden is forcibly imposed on an object.

In consideration of the problems, it is an object of the present invention to provide a technique for enlarging an imaging range without reducing a resolution in an object information acquiring apparatus for carrying out an image construction through a synthetic aperture.

Solution to Problem

The present invention provides an object information acquiring apparatus comprising:

a probe which is configured to carry out electronic scanning in a first direction in which a plurality of elements each transmitting an ultrasound wave to an object and outputting a receiving signal upon receipt of the reflected ultrasound wave is arranged;

a scanning unit which is configured to carry out mechanical scanning of the probe in a second direction intersecting with the first direction over a parallel plane with a receiving surface of each of the elements;

a first delay-and-sum unit which is configured to carry out a delay-and-sum in the first direction by using the receiving signal, thereby generating a first delay-and-sum signal;

a memory unit which is configured to store the first delay-and-sum signal in each position in the second direction for each sectional plane;

a selecting unit which is configured to select the first delay-and-sum signals corresponding to M sectional planes (M is an integer of two or more) from among the first delay-and-sum signals stored in the memory unit; and a second delay-and-sum unit which is configured to carry out a delay-and-sum in the second direction by using the selected first delay-and-sum signals corresponding to M sectional planes, thereby generating a second delay-and-sum signal, the second delay-and-sum signal output from the second delay-and-sum unit being used to acquire information in the object as image data, wherein the second delay-and-sum unit switches, in accordance with mechanical scanning of the probe, a first case in which a set of the M first delay-and-sum signals is fixed and a delay pattern is varied to carryout a second delay-and-sum and a second case in which the set of the M first delay-and-sum signals is varied and the delay pattern is fixed to carry out the second delay-and-sum, so as to generate the second delay-and-sum signal over the sectional plane positioned in a dead zone based on the first case.

Advantageous Effects of Invention

According to the present invention, it is possible to enlarge an imaging range without reducing a resolution in the object information acquiring apparatus for carrying out an image construction through a synthetic aperture.

Further features of the present invention will become apparent from the following description of exemplary embodiments with reference to the attached drawings.

BRIEF DESCRIPTION OF DRAWINGS

FIGS. 3A and 3B are flow charts for explaining a control according to Example 1 of the present invention.

FIGS. 5A to 5E are views for explaining a conventional synthetic aperture.

FIGS. 9A to 9G are views for explaining a transmission beam to be used in Example 3 according to the present invention.

FIGS. 10A to 10C are views for explaining a delay-and-sum in the first control phase according to the present invention.

DESCRIPTION OF EMBODIMENTS

A preferred embodiment according to the present invention will be described below with reference to the drawings. The present invention can be applied to an object information acquiring apparatus for transmitting/receiving an ultrasound wave in each position in which a probe is subjected to mechanical scanning and carrying out a delay-and-sum and a synthetic aperture by using a received signal. The object information acquiring apparatus utilizes an ultrasound echo technique for transmitting an ultrasound wave to an object and receiving a reflected wave reflected in the object (a reflected ultrasound wave), thereby acquiring object information as image data. The object information to be acquired indicates information which reflects a difference in an acoustic impedance of a tissue in the object.

In the following examples, description will be given to an ultrasound diagnostic imaging apparatus as an example of the object information acquiring apparatus.

Example 1

Figure 1:
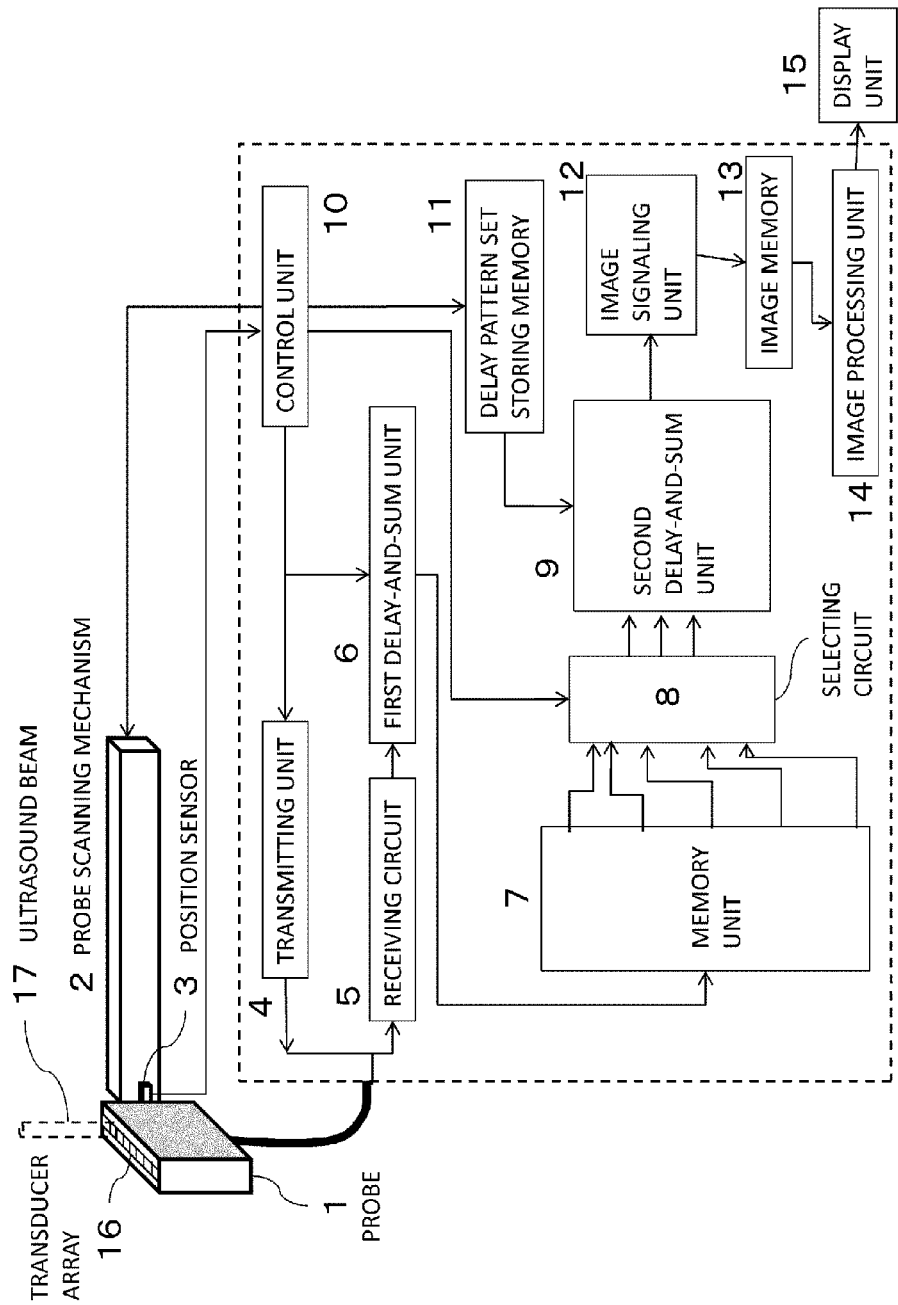
FIG. 1 is a diagram showing an example of a structure of an apparatus according to the present invention.

FIG. 1 shows a structure of an ultrasound diagnostic imaging apparatus based on the present invention. The apparatus includes a probe 1, a probe scanning mechanism 2, a position sensor 3, transmitting unit 4 (a transmitting circuit), a receiving circuit 5, a first delay-and-sum unit 6, memory unit 7, a selecting circuit 8, and a second delay-and-sum unit 9. The apparatus also includes control unit 10, a memory 11 for storing plural sets of delay patterns, image signaling unit 12, an image memory 13, image processing means 14 and display unit 15. Moreover, the reference numeral 16 denotes a transducer array included in the probe 1, and the reference numeral 17 denotes a conceptual view showing an ultrasound beam transmitted/received to/from the transducer array.

The present invention does not need to always include the display unit 15 such as an LCD or the image processing means 14. The present invention can also be constituted as an image acquiring apparatus having a function for carrying out electronic scanning for an ultrasound beam in the probe and mechanical scanning for the probe, thereby creating 3D ultrasound image data and storing the data in the image memory 13. In that case, the image processing means 14 is constituted by software over a general PC and can constitute a 3D rendering image, a sectional image or an MIP (Maximum Intensity Projection) image based on the 3D ultrasound image data by processing image data read from the image memory 13 in the image acquiring apparatus. In that case, moreover, it is also possible to add an interpolation between various image filters or pixels, a shape and coordinate transformation or a moving image processing.

An almost one-dimensional transducer array having elements arranged therein is present on the probe 1. Herein, it is sufficient that the almost one-dimensional transducer array is combined with the transmitting unit 4 and the first delay-and-sum unit 6 and an ultrasound transmitted/received beam carries out electronic scanning over a sectional slice surface to create a normal B mode ultrasound sectional image. More specifically, it is possible to use a 1D, 1.5D or 1.75D transducer array. Moreover, it is also possible to use a transducer array having a 2D structure which can scan a two-dimensional section through the electronic scanning in order to pick up a sectional slice image. In the present invention, a direction in which the electronic scanning is carried out by using a plurality of elements is referred to as a first direction. In the 1D array transducer, the electronic scanning is carried out in an array direction of the element. For this reason, a direction in which a plurality of elements is arranged is coincident with the first direction.

As the electronic scanning of the probe 1, there is used sector scanning for changing a direction of an ultrasound transmitted/received beam to electronically scan the ultrasound transmitted/received beam in a fan shape over a plane, linear scanning for electronically scanning an ultrasound transmitted/received beam over a plane through an almost parallel movement, or the like. The linear scanning will be mainly described below and the present invention is not restricted thereto. The linear scanning has advantages that an imaging width based on the electronic scanning is constant, a wide imaging region is obtained also in a probe proximity part to be an imaging target, a lateral resolution does not depend on an imaging depth (a depth measured from a probe and imaging target bonding surface), and the like. Therefore, the linear scanning can be advantageously applied to an ultrasound mammography.

The probe 1 is fixed to a movable portion (not shown) of the probe scanning mechanism 2 and is moved, together with the movable portion, in an almost perpendicular direction to the sectional slice image to be subjected to the electronic scanning. It is apparent that this direction intersects with the first direction to be the electronic scanning direction over a parallel plane with a receiving surface of the element. The movement is referred to as mechanical scanning. The probe scanning mechanism 2 moves the movable portion through a motor driving operation in accordance with a control to be carried out by the control unit 10. At the same time, a position of the probe 1 is detected by the control unit 10 through the position sensor 3 fixed to the movable portion, for example. In the present invention, it is sufficient that the control unit 10 can carryout a control depending on the position of the probe 1. For this reason, it is also possible to omit the position sensor 3 if a driving control is enabled by using a high precision stepping motor in a driving operation. A mechanical scanning direction in which the probe 1 is moved (which is also referred to as an elevation direction) corresponds to the second direction according to the present invention. The sectional slice image acquired in the present invention is perpendicular to a surface defined by the first direction and the second direction.

The probe 1 carries out an ultrasound transmitting/receiving operation to acquire sectional slice image data of an ultrasound echo while it is moved by the probe scanning mechanism 2. The sectional slice image data thus acquired is stored in the image memory 13. The sectional slice image data stored in the image memory 13 is processed into a desirable sectional slice image for an object, a 3D rendering image or the like by the image processing unit 14 and the image is thus displayed on the display unit 15 after the end of the mechanical scanning or during the mechanical scanning through the probe scanning mechanism 2. In particular, the sectional slice image data according to the present invention features that a delay-and-sum using a synthetic aperture principle is executed in the moving direction of the probe 1 (the second direction) as will be described below. Thus, three-dimensional image data can be obtained by the apparatus.

Moreover, the control unit 10 controls the start or stop of the movement of the probe 1 through the probe scanning mechanism 2 synchronously with the operation for transmitting/receiving an ultrasound wave, or a moving speed, thereby acquiring sectional slice image data in a desirable position.

Referring to the mechanical scanning of the probe 1, there are a step and repeat method and a continuous scanning method, and they can also be combined with each other. The step and repeat method serves to intermittently move and stop the probe 1 and to electronically scan the ultrasound beam 17 for a stopping period of the probe 1, thereby acquiring sectional slice data. The continuous scanning method serves to acquire the sectional slice data while moving the probe 1 almost continuously.

When the probe 1 reaches a predetermined position by the probe scanning mechanism 2, the control unit 10 starts to electronically scan the ultrasound beam 17.

In that case, the transmitting unit 4 first drives at least a part of the transducer array 16 on the probe 1, thereby transmitting the transmitted ultrasound beam 17 toward the object. The transmission beam can be formed by a well-known method. A transducer element corresponding to a transmitting aperture on the transducer array 16 is selected by the control unit 10 so that the ultrasound transmission beam 17 having a transmission focus is transmitted.

The ultrasound transmission beam 17 generates an ultrasound reflected wave depending on an acoustic impedance of each portion during a propagation in the object and a part of the ultrasound reflected wave is received as an ultrasound received echo by the transducer array 16. When the ultrasound received echo is received by each transducer element selected on the transducer array 16, each received signal (an analog signal) is generated and output to the receiving circuit 5. The receiving circuit 5 is constituted by an amplifying circuit and an AD converter, amplifies each received signal which is input, and converts the amplified signal into digital time series data (the received signal which is digitized). At this time, by selecting a plural sets of transducer elements which are chosen through a switching circuit, it is possible to determine a region for receiving an ultrasound wave over the transducer array 16, that is, a position and size of a receiving aperture.

A plurality of analog signals received from each transducer element corresponding to a receiving aperture which is provided on the transducer array 16 is converted into the same number of received digital time series data through the receiving circuit 5 and the same data is then input to the first delay-and-sum unit 6. The first delay-and-sum unit 6 creates an ultrasound received beam signal (a first delay-and-sum signal) by using the received digital time series data.

Figure 2A:
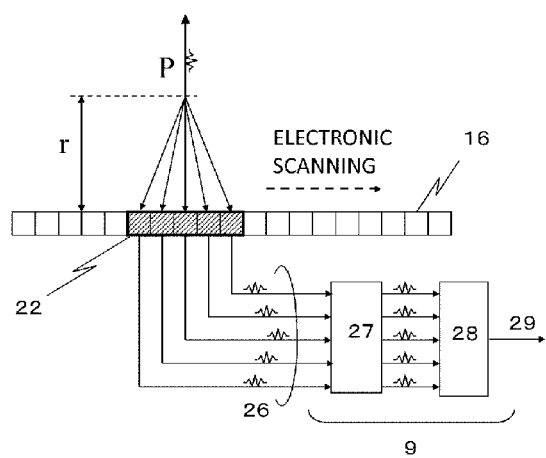
FIGS. 2A and 2B are views for explaining an ultrasound received beam signal according to the present invention.
Figure 2B:
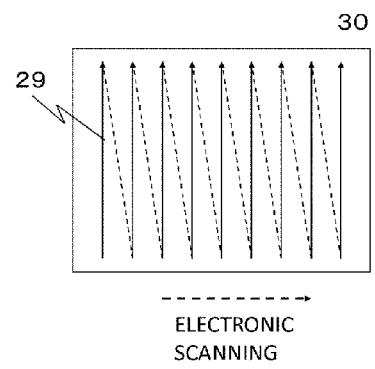

FIG. 2A is a view for explaining the creation of the ultrasound received beam signal and FIG. 2B is a view schematically showing a position that a scanning signal represented by the ultrasound received beam signal takes over a sectional slice surface (a sectional plane).

In the drawings, it is assumed that an ultrasound transmission beam is reflected on a point P in a position placed from the closest element by a distance r and the reflected wave is received by the transducer array 16. A received signal 26 output from each transducer element is shifted in a time depending on a propagation distance of the reflected wave. In other words, an ultrasound echo reflected on the point P is received with a gradual delay from a central position of a transducer element group constituting an aperture (which is referred to as an aperture element group) 22 toward an outside element. Therefore, a delay time of the received signal 26 of each transducer element in the aperture element group 22 is adjusted by a delay adjusting circuit 27 on the basis of a signal received in the central position. When an echo signal component from the point P included in each received signal 26 is added by an addition circuit 28, then, it is possible to receive a strong signal setting the point P to be a focal point. Ultrasound echoes sent in various directions are superposed and received by the transducer element. Even if the ultrasound echo from the other point is added, a phase of the received wave is not aligned. For this reason, a large signal component cannot be obtained. Moreover, the delay adjusting circuit 27 and the addition circuit 28 are included in the first delay-and-sum unit 6.

The time t that the reflected wave sent from the point P at the distance r is received in the central position of the aperture element group 22 is expressed in $t=2r/c$, wherein a known sound speed is represented by c. Accordingly, the distance r to a corresponding reflection position can be calculated based on the time t, and a signal delay time of each element can be calculated based on the calculated r. If a proper adjustment of the delay time corresponding to the distance r is carried out by the delay adjusting circuit 27 depending on the receiving time t, accordingly, it is possible to form a one-dimensional reflecting signal waveform which is focused on all points and is strong. This is referred to as a receiving dynamic focus. As a result, a region having a high receiving sensitivity of the ultrasound reflecting echo, that is, a received beam is formed in a region provided along a path for the transmission beam. An output of the first delay-and-sum unit 6 is an ultrasound received beam signal 29 obtained by adding a received signal caused by a received beam.

The ultrasound received beam signal 29 (the first delay-and-sum signal) output from the first delay-and-sum unit 6 is sequentially stored in the memory unit 7 with electronic scanning. At this time, a signal is stored for each sectional plane in the memory unit 7.

As shown in FIG. 2B, the ultrasound received beam signal 29 is output in a raster scanning form through the electronic scanning. Consequently, it is possible to acquire an ultrasound echo signal for a sectional slice surface 30. In other words, the ultrasound received beam signal 29 (the first delay-and-sum signal) is a scanning line signal for electronic beam scanning with respect to the sectional slice surface 30.

The addition to be carried out by the adding circuit 28 can also include an apodizing processing for weighting each input signal to execute the addition. The apodizing processing has an effect for controlling a receiving aperture or decreasing an influence of an interference wave from a periphery. The weight may be fixed to meet a purpose or may be changed depending on a receiving time.

The control unit 10 controls an ultrasound transmission/receipt in order to acquire the ultrasound received beam signal 29 corresponding to a scanning line signal over the sectional slice surface 30 through the serial electronic scanning, and controls a movement of the probe 1 through the probe scanning mechanism 2.

With the movement of the probe 1, the ultrasound received beam signals 29 corresponding to the scanning line signal over the sectional slice surfaces in different positions are stored in the memory unit 7.

The second delay-and-sum unit 9 carries out a second delay-and-sum processing for enhancing a function in the elevation direction (the second direction) based on a synthetic aperture method with respect to the ultrasound received beam signals 29 acquired respectively when the probe 1 is placed in different positions. The selecting circuit 8 selects a set of ultrasound received beam signals 29 stored in the memory unit 7 and inputs the set to the second delay-and-sum unit 9. A set of delay amounts to be given to the ultrasound received beam signal 29 for using the second delay-and-sum processing is stored in the delay pattern set storing memory 11.

As one of features of the present invention, the set of ultrasound received beam signals 29 to be input to the second delay-and-sum unit 9 and the set of delay patterns to be used are changed depending on the probe position for probe mechanical scanning. The change is divided into first to three control phases.

The first control phase serves to fix the set of ultrasound received beam signals to the input in parallel with the second delay-and-sum unit depending on the probe position immediately after the start of the probe mechanical scanning and to change the delay pattern to be selected, thereby executing the second delay-and-sum processing.

The second control phase serves to change the set of ultrasound received beam signals to be input to the second delay-and-sum unit and to fix the delay pattern to be selected, thereby executing a delay-and-sum to be carried out through the second delay-and-sum unit.

The third control phase is a processing to be carried out for a period immediately before the end of the probe mechanical scanning, and serves to execute the same processing as the first control phase in a reverse direction to an advancing direction of the probe.

The first control phase and the third control phase correspond to a first case according to the present invention. The second control phase corresponds to a second case according to the present invention. In the present example, the first and third control phases represent a period for which an imaging plane of a region to be a dead zone is obtained in the conventional synthetic aperture processing. The first to third control phases will be described below in detail.

A result of the delay-and-sum carried out through the second delay-and-sum unit 9 is output to the image signaling unit 12. The image signaling unit 12 performs an amplitude detection and down-sampling using an envelope demodulation or the Hilbert transformation in order to convert the ultrasound echo signal subjected to the delay-and-sum into a luminance signal depending on a strength, and furthermore, to modulate a signal band into a frequency band which is suitable for image data. An LOG compression may be carried out to obtain a dynamic range of a luminance. Moreover, it is also possible to provide various filters for an image signal.

An image signal created by the image signaling unit 12 is stored in the image memory unit 13.

(Control Flow)

A control processing related to the delay-and-sum which is to be carried out by the control unit 10 according to the present example will be described with reference to FIG. 3. FIG. 3A is a flow chart showing the whole processing, giving explanation from a start of a 3D image data acquisition to an end thereof. FIG. 3B is a flowchart for explaining a processing for electronically scanning each sectional slice surface to acquire a plurality of ultrasound received beam signals corresponding to scanning line signals over a plane in FIG. 3A (which is referred to as a sectional scanning line processing).

At Step S301, the probe scanning mechanism 2 starts the mechanical scanning of the probe 1. When the probe 1 reaches a predetermined position, an ultrasound wave is started to be transmitted/received.

At Step S302, the probe 1 starts the electronic scanning. Subsequently, the mechanical scanning and the electronic scanning of the probe are successively executed.

At Step S303, the first delay-and-sum unit 6 carries out a delay-and-sum over digital time series data which is received, and generates the ultrasound received beam signal 29 as a first delay-and-sum signal.

At Step S304, the ultrasound received beam signal 29 thus obtained is stored in the memory unit 7. The ultrasound received beam signal 29 corresponding to each ultrasound beam scanned with the electronic scanning is sequentially stored in the memory unit 7. The above processing is repeated so that the processing proceeds to the first control phase in a stage in which the ultrasound received beam signals 29 corresponding to a predetermined number, that is, M sectional slice surfaces which will be described below are stored (Step S305=YES). In respect of a property of a synthetic aperture, it is apparent that M is an integer of two or more.

When the first control phase is started, at Step S306, the selecting circuit 8 selects a set of the ultrasound received beam signals 29 to be input to the second delay-and-sum unit 9. At this time, the ultrasound received beam signal 29 constituting the scanning line signal on the sectional slice surface is selected by the selecting circuit 8 and is input to the second delay-and-sum unit 9 in order of the electronic scanning.

At Step S307, a set of delay patterns to be performed in the second delay-and-sum unit 9 is selected from the delay pattern set storing memory 11.

At Step S308, the second delay-and-sum unit 9 executes a synthetic aperture processing for carrying out a delay-and-sum in an elevation direction in the selected delay pattern, thereby generating a second delay-and-sum signal and outputting the second delay-and-sum signal to the image signaling unit 12. Then, the electronic scanning related to a next sectional slice surface is carried out with the movement of the probe 1 to acquire the ultrasound received beam signal 29 over the sectional slice surface.

FIG. 3B shows the details of a signal acquisition related to the sectional slice surface at Step S309 (a sectional scanning line processing).

At Step S401, there is set a delay pattern to be used in the first delay-and-sum unit 6. In the case in which the electronic scanning for the sectional slice surface is linear scanning, particularly, it is sufficient that the delay pattern of the received ultrasound beam to be used in the first delay-and-sum unit 6 is constant. For this reason, the delay pattern to be used in the first delay-and-sum unit 6 may be previously set in a lump at the start of the first control phase, for example.

After Step S402, the transducer array of the probe starts the electronic scanning. More specifically, at Step S403, actual electronic scanning is carried out and the ultrasound beam thus scanned is output. At Step S404, the first delay-and-sum unit sequentially creates the ultrasound received beam signal 29. At Step S405, the created signal is stored in the memory unit 7.

After the Step S309, the processing returns to the Step S307 again in which the set of the delay pattern to be carried out in the second delay-and-sum unit 9 is selected again.

Then, there is repeated an operation for executing the delay-and-sum in the elevation direction by using a different delay pattern, outputting a result to the image signaling unit 12 and thereafter carrying out the sectional scanning line processing with the movement of the probe 1.

As described above, in the first control phase, there is carried out a control for fixing a set of input signals to the second delay-and-sum unit 9 with the movement of the probe 1 and changing the delay pattern to be used. The first control phase is continuously carried out until a predetermined number of sectional slice surfaces are acquired after the mechanical scanning of the probe is started.

After the first control phase is ended, the control unit 10 starts the second control phase.

At Step S310, the delay pattern for the delay-and-sum in the elevation direction which is to be carried out by the second delay-and-sum unit 9 is read from the delay pattern set storing memory 11 and is thus set.

At Step S311, the selecting circuit 8 selects the set of ultrasound received beam signals 29 corresponding to the sectional slice surface to be used in a synthetic aperture from the memory unit 7 and sets the set as data to be input to the second delay-and-sum unit 9.

At Step S312, the second delay-and-sum unit executes the delay-and-sum in the elevation direction by setting, as an input, the set of ultrasound received beam signals 29 which is selected, and outputs a result to the image signaling unit 12. This is a synthetic aperture processing of the phase.

Subsequently, the sectional scanning line processing is carried out at Step S313 with the movement of the probe 1. The ultrasound received beam signal 29 corresponding to a new sectional slice surface thus created is stored in the memory unit 7. In a state in which the delay pattern for the delay-and-sum in the elevation direction is maintained to be fixed, the set of ultrasound received beam signals 29 corresponding to the sectional slice surface to be used for the synthetic aperture is newly selected by the selecting circuit 8 and the second delay-and-sum is carried out by the second delay-and-sum unit 9. Furthermore, there is repeated the execution of the sectional scanning line processing for acquiring the ultrasound received beam signal 29 corresponding to a next sectional slice surface.

As described above, in the second control phase, there is carried out a control for fixing the delay pattern and varying the set of a signal to be input to the second delay-and-sum unit 9 with the movement of the probe 1.

At Step S314, then, the movement of the probe is ended when an ending point of a probe mechanical scanning region is reached.

Thereafter, the processing proceeds to the third control phase. Herein, the ultrasound received beam signal 29 constituting the scanning line signal over the sectional slice surface is not acquired newly. By using the ultrasound received beam signals 29 stored in the memory unit 7, the processing is carried out by the second delay-and-sum unit.

At Step S315, the set of ultrasound received beam signals 29 to be used is selected by the selecting circuit 8.

At Step S316, a set of delay patterns to be carried out by the second delay-and-sum unit 9 is selected.

At Step S317, the delay-and-sum in the elevation direction is carried out by using the selected delay pattern (the synthetic aperture processing) and a result is output to the image signaling unit 12. The processing is repeated at a predetermined number of times while the delay pattern to be selected is varied.

In the control phase, it is not necessary to create a new ultrasound received beam signal 29. Therefore, it is not necessary to carry out the sectional scanning line processing including an ultrasound transmission and it is preferable to carry out a control in order to omit these operations.

When a final synthetic aperture processing is ended, the collection of 3D ultrasound image data in accordance with the mechanical scanning of the probe is ended.

(Synthetic Aperture Effect)

Next, a synthetic aperture effect obtained by the delay-and-sum processing to be carried out through the second delay-and-sum unit will be described with reference to FIGS. 4 and 10. Herein, description will be given by taking, as an example, the case of linear scanning. Although sizes of transmitting and receiving apertures are set to be equal to each other for simplicity of explanation, the sizes of the transmitting and receiving apertures may be different from each other.

Figure 4A:
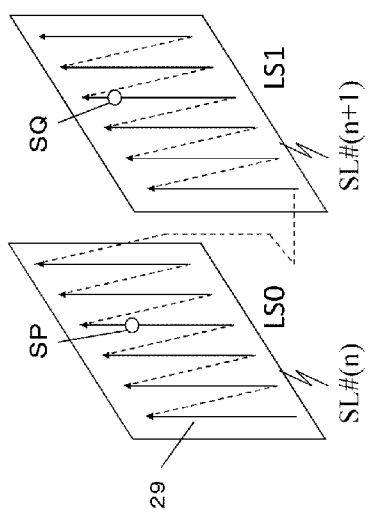
FIGS. 4A to 4C are views for explaining a delay-and-sum in a first control phase according to the present invention.

First of all, description will be given, with reference to FIG. 4A, to the fact that an equivalent delay-and-sum to a two-dimensional array is enabled through a delay-and-sum in two stages having the first delay-and-sum unit 6 and the second delay-and-sum unit 9. For simplicity of explanation, it is assumed that a remarkable point P for carrying out a synthetic aperture is present in a plane of a sectional slice SL#(n).

An ultrasound bream emitted vertically from a center S0 of an aperture present on an almost one-dimensional array transducer is reflected on a P point, and is received by a transducer element in an R0 position. Next, the probe is moved to a position of a sectional slice SL#(n+1) and emits an ultrasound beam again by setting a position S1 corresponding to S0 as an aperture center. Although the ultrasound beam is emitted in a vertical direction, a part thereof is also propagated in a direction of the P point in the sectional slice surface SL#(n) and an ultrasound wave reflected on the P point is received on a point R1 corresponding to the R0 point. By adding a signal received on R0 and a signal received on R1 through an adjustment of a shift in a receiving time corresponding to a propagating time from a transmission to a receipt through the reflection on the P point, it is possible to implement a delay-and-sum based on the synthetic aperture principle.

For example, it will be considered that an image of the point P is constituted on the sectional slice surface SL#(n). In this case, by adjusting a shift of a receiving time corresponding to a propagating time and adding the shift to the signals in S1 and R1 positions as well as the signals obtained by the transducer element in the one-dimensional positions of S0 and R0, it is possible to enhance a resolution in a vertical direction of the sectional slice surface which is equivalent to a two-dimensional array. Herein, description will be given by using an example in which four receiving points are present. Even if the number of the receiving points is more increased, the same principle is applied. In the delay-and-sum, it is sufficient to give respective propagation distance s and a time required for propagating a difference between R0-P, S1-P and R1-P by an ultrasound wave, as a delay, to the signals received in the positions R0, S1 and R1 based on the shortest propagation distance S0-P. Hereinafter, the target point P constituting an image through the synthetic aperture will be referred to as a focal point of the synthetic aperture.

After the signals in the S0 and R0 positions are acquired by the almost one-dimensional array probe, the probe is subjected to the mechanical scanning to acquire the signals in the S1 and R1 positions. In that case, the first delay-and-sum unit 6 first carries out a delay-and-sum for the signals in the S0 and R0 positions and then carries out a delay-and-sum for the signals in the S1 and R1 positions. The former gives a delay to the signal in the R0 position based on the propagation distance S0-P and the latter gives a delay to the signal in the R1 position based on the propagation distance S1-P. Thereafter, it is sufficient to carry out the delay-and-sum based on the synthetic aperture over these results through the second delay-and-sum unit 9.

In more detail, the delay-and-sum for the signal in the S1 and R1 positions is carried out through the first delay-and-sum unit 6 based on the propagation distance S1-P, and the delay-and-sum for the signals in the S0 and R0 positions is carried out based on the propagation distance S0-P. Accordingly, an ultrasound propagation time corresponding to a difference between the propagation distances S1-P and S0-P is given as a delay to a former addition result and they are added to the latter. Consequently, the first delay-and-sum is carried out on the signals on four points based on the propagation distance S0-P.

At this time, there will be considered a point Q placed at an equal distance from S1 to P in a vertical direction in the sectional slice surface SL#(n+1) from the point S1. In this case, a triangle formed by the points S1, P and R1 and a triangle formed by the points S1, Q and R1 are apparently congruent. Therefore, a time required for reaching R1 from S1 via the P point is equal to a time required for reaching R1 from S1 via the Q point. This relationship is common to the transducer element in the R1 position as well as the other transducer elements of the same almost one-dimensional transducer array. In the position of the sectional slice surface SL#(n+1), accordingly, a one-dimensional delay-and-sum result with the P point set to be a focal point and a delay-and-sum result with the Q point set to be a focal point are entirely the same addition signals. In the two-dimensional delay-and-sum for the P point, therefore, it is apparently preferable to first carry out the delay-and-sum for each sectional slice surface, thereby obtaining delay-and-sum signals on the points P and Q and to then carry out the delay-and-sum in the elevation direction, thereby adding the delay-and-sum signals on the points P and Q.

If a receiving dynamic focus is to be carried out by the first delay-and-sum unit 6, particularly, a delay-and-sum in an array direction of the almost one-dimensional transducer array is carried out on each of the sectional slice surfaces depending on a height of the target point. For example, a delay is given to the signals sent from the R0 and R1 positions depending on the heights of the points P and Q respectively, and the signals are added to the signals sent from the S0 and S1 positions. Therefore, a delay processing can be carried out by the first delay-and-sum unit 6 independently of a delay processing to be carried out by the second delay-and-sum unit 9. Accordingly, the ultrasound received beam signal 29 subjected to the delay-and-sum through the first delay-and-sum unit 6 is stored as a scanning line signal on the sectional slice surface in the memory unit 7. Then, the probe 1 is moved to carry out the second delay-and-sum between the ultrasound received beam signals 29 acquired on the different sectional slice surfaces. Thus, it is possible to obtain the synthetic aperture effect described above.

Figure 4B:
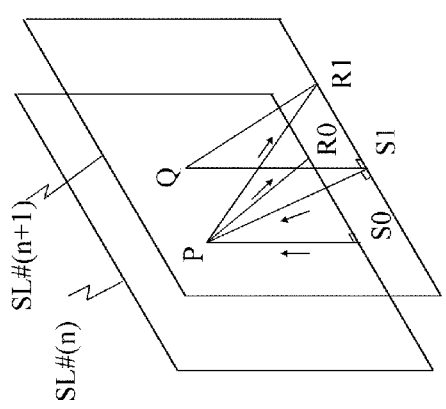

FIG. 4B shows a state in which the ultrasound received beam signals 29 obtained by the first delay-and-sum unit 6 form a scanning line on the sectional slice surfaces SL#(n) and SL#(n+1) in a raster scanning form as described above. In conformity with FIG. 4A, the ultrasound received beam signal 29 corresponding to the scanning line on the sectional slice surface is acquired by the first delay-and-sum unit 6 while the almost one-dimensional transducer array is scanned from (a position including) S0 to S1. Subsequently, a signal for a scanning line on the sectional slice surface SL#(n+1) is acquired while the transducer array is moved to S2 (not shown) in the same manner.

In FIG. 4B, LS0 and LS1 represents a scanning line signal corresponding to the positions of the points S0 and S1, and ultrasound echo portions SP and SQ corresponding to the points P and Q are present on the signals. Positions of the scanning lines indicated in LS0 and LS1 are obtained by a parallel translation with the movement of the probe 1, which will be referred to as a scanning line corresponding over the sectional slice surface depending on the mechanical scanning of the probe. SP and SQ are subjected to the delay-and-sum of the receiving dynamic focus for the aperture in the direction of the sectional slice surface through the first delay-and-sum unit 6. The receiving dynamic focus is carried out. Therefore, temporal positions corresponding to a depth direction in the scanning line signals LS0 and LS1 formed by the ultrasound received beam signal 29 correspond to a double of values obtained by dividing lengths S0-P and S1-P=S1-Q by a sound speed c, respectively. S1-Q is obtained based on a geometrical relationship from a length between positions of the points S1 and S2 (that is, an interval between the sectional slice surfaces SL#(n) and SL#(n+1)) and the length of S0-P. For this reason, if there is determined the position of SQ on the scanning line signal LS1 corresponding to SP in an optional position on the scanning line signal LS0, it is preferable to give a delay to the scanning line signal LS1 in such a manner that both of them are coincident with each other. By giving the delay to SQ on LS2 corresponding to the optional SP on LS0 to carry out an addition, thus, it is possible to carry out a receiving dynamic focus also in the elevation direction.

In the second delay-and-sum unit 9, it is sufficient to select the ultrasound received beam signals 29 constituting the scanning line signal of the scanning line corresponding over the sectional slice surface, thereby carrying out the first delay-and-sum with respect to the ultrasound received beam signals 29 output from the first delay-and-sum unit 6. The delay to be given at this time is determined by an interval between the sectional slice surfaces and a position in the depth direction of a focal point.

For simplicity, the description has been given on the assumption that the position of the focal point P of the synthetic aperture is placed on the sectional slice surface. However, the focal point P of the synthetic aperture does not need to be placed on the sectional slice surface. In other words, the focal point of the synthetic aperture may be provided between the respective sectional slice surfaces acquired by the electronic scanning of the almost one-dimensional transducer or a position placed out of the sectional slice surface. Also in this case, it is possible to execute the second delay-and-sum in the elevation direction by using the geometrical relationship from the focal point P and the position of each sectional slice surface.

In the present invention, thus, a processing for giving a delay to a large number of signals to carry out an addition is first executed over the almost one-dimensional array. Then, a delay and an addition processing for the result are carried out in an elevation moving direction. Thus, the structure has the two-stage delay-and-sum unit. Accordingly, it is possible to control and reduce a circuit scale for a real-time processing as compared with the case in which a general two-dimensional array is used, and furthermore, the case in which all received signals are stored in a memory and a synthetic aperture is then carried out.

(First Control Phase)

The details of the synthetic aperture in the first control phase will be described with reference to FIGS. 10A to 10C. The second delay-and-sum is determined by a position of each sectional slice surface and that of a target point. Therefore, the drawings are projection views into a section created in an elevation direction in which the probe 1 is moved and a depth direction of an object. In the present example, the first control phase indicates a period for which an imaging plane to be sectional slice image data in a region serving as a dead zone is obtained in the conventional synthetic aperture processing together with a third control phase which will be described below.

The dead zone according to the present invention will be described. The dead zone represents a region which is not subjected to the synthetic aperture (a region in which sectional slice image data having a high resolution through the second delay-and-sum cannot be generated) in the case in which the second delay-and-sum is carried out in a mechanical scanning direction with a delay pattern of the second delay-and-sum fixed as in the related art. In other words, in the case in which only the second control phase is carried out to execute the second delay-and-sum irrespective of the position of the mechanical scanning, the dead zone is a region which is not subjected to the delay-and-sum by using ultrasound received beam signals corresponding to M sectional planes. The number of the sectional planes to be used in the execution of the second delay-and-sum in a mechanical scanning direction is set to be M.

In the drawing, SL#(0) to SL#(8) are sectional slice surfaces corresponding to the position of the probe 1. FP1 to FP3 indicate imaging planes on which focal points P1 to P3 for giving a focus as a target of the synthetic aperture are provided. In the following description, the imaging plane is used as meaning of sectional slice image data to be generated by the synthetic aperture. The sectional slice surface is determined according to the mechanical scanning of the probe 1. In particular, the sectional slice surface SL#(0) is set to be a probe mechanical scanning starting position.

The reference numeral 40 denotes an ultrasound propagation path for obtaining a delay amount to be given by the second delay-and-sum unit 9. The reference numeral 41 denotes an auxiliary line connecting points in which an ultrasound propagation time is equal. Moreover, the ultrasound received beam signal 29 to be stored in the memory unit 7 is illustrated on a conceptual view basis by using a circle mark. The respective circle marks represent the ultrasound received beam signals 29 corresponding to scanning line signals in the respective sectional slice surfaces in a lump. Hereinafter, description will be given on the assumption that the mechanical scanning is continuous.

FIG. 10A illustrates a stage in which the ultrasound received beam signals 29 corresponding to a predetermined number M of combined sectional slice surfaces are stored after the start of the mechanical scanning of the probe 1 and the processing proceeds to the first control phase. It is sufficient that the predetermined number M is taken as the number of sectional slice surfaces to be used in the execution of the synthetic aperture in the elevation direction, and is determined by a size of the aperture and a pitch of the sectional slice surface in the synthetic aperture in the elevation direction. With an increase in M, generally, a resolution in a synthetic aperture effect is enhanced and the processing of the second delay-and-sum unit 9 is increased. In this example, M=5 is set.

When a pitch interval between the sectional slice surfaces is reduced, an elevation resolution is enhanced, while a whole imaging time is prolonged. Herein, it is assumed that the pitch interval between the sectional slice surfaces is equal. This is preferable for a structure in which a mechanical scanning speed of the probe 1 is caused to be equal and a pitch in the elevation direction of 3D image data to be stored in the image memory 13 after the processing through the image signaling unit 12 in a second stage is caused to be uniform, and suitable data for a subsequent image processing can be generated. However, the pitch interval between the sectional slice surfaces may be varied by the control unit 10 for the purpose of an enhancement in a partial resolution in an imaging region or the like.

In FIG. 10A, the memory unit 7 stores the ultrasound received beam signals 29 corresponding to five sectional slice surfaces of SL#(0) to SL#(4). FIGS. 10B and 10C show a stage in which the ultrasound received beam signals 29 corresponding to the respective sectional slice surfaces which are acquired with the movement of the probe 1 are successively stored in the memory unit 7. In FIGS. 10A to 10C, the ultrasound received beam signal 29 acquired newly and stored depending on the movement of the probe 1 is displayed in a black circle mark. The ultrasound received beam signals 29 corresponding to the sectional slice surfaces SL#(0) to SL#(4) selected by the selecting circuit 8 are input to the second delay-and-sum unit 9. At the same time, there is selected any of the delay patterns stored in the delay pattern set storing memory 11 which corresponds to time phases in FIGS. 10A to 10C, and the second delay-and-sum is carried out by the second delay-and-sum unit 9.

The delay pattern is determined and selected in the following manner.

In FIG. 10A, FP1 denotes an imaging plane to be synthesized by the synthetic aperture. In particular, FIG. 10A shows a time phase in which the delay-and-sum to be carried out by the second delay-and-sum unit is started. Therefore, the plane (FP1) corresponds to an imaging start surface. A position in an elevation direction of FP1 is determined by an imaging range to be acquired. As shown in the drawing, the imaging plane can be taken out of the mechanical scanning range. Similarly, FP2 and FP3 denote imaging planes to be synthesized through the synthetic aperture in the time phases of FIGS. 10B and 10C. Intervals in the elevation direction of FP1 to FP3 are caused to be coincident with pitches of the sectional slice surfaces SL#(0) to SL#(4). This is suitable for a creation of image data at an interval which is matched with an interval between imaging planes obtained in the second control phase which will be described below, and is a preferable structure for a resolution in the elevation direction or the utilization of image data. However, the other intervals may be used.

First of all, description will be given to a delay-and-sum processing for carrying out focusing on the focal point P1 on FP1 in FIG. 10A. The delay-and-sum processing is carried out based on a scanning line corresponding to P1 on the sectional slice surfaces SL#(0) to SL#(4). The focal point P1 is present on FP1 and a line where a scanning line on the sectional slice surface is moved in parallel in a reverse direction to a direction in which the probe 1 is moved. The line on which P1 is provided will be referred to as an imaging line on FP1.

The ultrasound propagation path 40 indicates each propagation path for ultrasound waves from a center of an ultrasound aperture to the focal point P1 in the creation of a scanning line to which the sectional slice surface on SL#(0) to SL#(4) corresponds. The length is geometrically obtained as a length of a hypotenuse of a right angled triangle in which a vertical distance between each of SL#(0) to SL#(4) and FP1 is set to be a base and a height of the focal point P1 is set to be a height. The delay-and-sum in the elevation direction is carried out by giving a delay to a signal on a scanning line to which the sectional slice surface on SL#(0) to SL#(4) corresponds in order to offset a difference between propagation times of respective paths in the ultrasound propagation path 40, thereby executing an addition.

The auxiliary line 41 is a circle with the focal point P1 set to be a center. Based on each of the paths in the ultrasound propagation path 40 and an intersection point of the circle, it is possible to geometrically calculate a difference between respective ultrasound propagation path lengths. By using the difference between the propagation path lengths and the sound speed c, it is possible to calculate a delay amount to be given to the scanning line to which the sectional slice surface on SL#(0) to SL#(4) corresponds. By using the delay amount, it is possible to carryout the delay-and-sum for the focal point P1. When the height of the focal point P1 on the imaging plane FP1 is varied, a signal subjected to the delay-and-sum with respect to each point on the imaging line is obtained.

A scanning direction of the probe 1 is equivalent to an almost vertical direction of the sectional slice surfaces SL#(0) to SL#(4). For this reason, when a scanning line corresponding to an imaging line on the imaging plane FP1 for each of the sectional slice surfaces SL#(0) to SL#(4) is selected and the delay amount is given to a scanning line group thus selected, thereby executing the delay-and-sum, a delay-and-sum signal for each point on the imaging line is obtained. There is obtained the delay-and-sum signal subjected to the synthetic aperture in the elevation direction by using the sectional slice surfaces SL#(0) to SL#(4) for each point on each imaging line in the imaging plane FP1.

The delay amount to be given at this time is determined by the height of the focal point P on the imaging line and a decision whether the scanning line is provided on any of the sectional slice surfaces SL#(0) to SL#(4). For the scanning line on the same sectional slice surface, it is possible to use the same set of delay amounts. It is sufficient that the set of delay amounts determined by the height of the focal point and the sectional slice surface is stored as a delay pattern in the delay pattern set storing memory 11. In the first control phase, the delay pattern of the second delay-and-sum unit 9 is selected from the delay pattern set storing memory 11 depending on the scanning position of the probe 1. The delay pattern thus selected is processed by the second delay-and-sum unit 9.

As described above, there is obtained the delay-and-sum signal subjected to the synthetic aperture for each point on the imaging line over the imaging plane FP1. The delay-and-sum signal thus obtained is subjected to image signaling through the image signaling unit 12 and the image signal is stored in the image memory 13. Consequently, the sectional slice image data subjected to the synthetic aperture corresponding onto the imaging plane FP1 is stored in the image memory 13.

The cases of FIGS. 10B and 10C are also the same. In other words, a delay pattern taken for each of the imaging planes FP2 and FP3 in accordance with the mechanical scanning of the probe 1 is calculated based on the geometrical arrangement of the sectional slice surfaces SL#(0) to SL#(4) and the imaging planes FP2 and FP3. A result of the calculation is stored in the delay pattern set storing memory 11. When the probe 1 is moved to reach the time phases in FIGS. 10B and 10C, the control unit 10 gives each delay pattern to the second delay-and-sum unit 9 through the delay pattern set storing memory 11. A result obtained by executing the delay-and-sum in the elevation direction is stored, in the image memory 13, as sectional slice image data subjected to the synthetic aperture corresponding to the imaging planes FP2 and FP3.

By the method described above, as shown in FIGS. 10A to 10C, the synthetic aperture on the imaging planes FP1 to FP3 is carried out together in accordance with the mechanical scanning of the probe 1. A signal value obtained as a result is converted into an image signal through the image signaling unit 12 and the image signal is stored, in the image memory 13, as sectional slice image data for each of the imaging planes FP1 to FP3. By changing the delay pattern to carry out the second delay-and-sum, thus, it is possible to generate the second delay-and-sum signal on the sectional plane positioned in the dead zone. Therefore, the dead zone can be reduced. Away for setting the imaging planes FP1 to FP3, a way for setting an image line on the imaging plane, or the like is optional depending on handling of image data. However, it is preferable to carry out a coincidence with a pitch of the mechanical scanning of the probe 1 or a pitch of the electronic scanning of the ultrasound beam over the sectional slice surface and with a pixel or a voxel of a desirable image through the image processing unit 14 in the subsequent stage.

(Example of Specific Structure of Second Delay-and-Sum Unit)

Figure 4C:
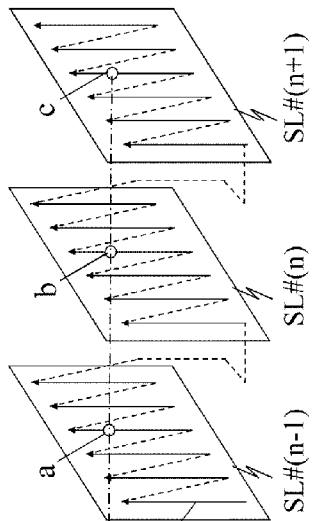

With reference to FIG. 4C, the processing of the second delay-and-sum unit will be described in more detail. FP in the drawing indicates an imaging plane to carry out a synthetic aperture delay-and-sum in an elevation direction. FL denotes an imaging line to be a target on the imaging plane FP and F0 denotes a focal point on the imaging line. FIG. 4C shows the scanning order of the ultrasound received beam signal 29 to be output when the sectional slice surface is output in order of . . . , SL#(n−1), SL#(n), SL#(n+1), . . . , while the probe 1 is continuously moved in the elevation direction in the same manner as FIG. 4B.

In an inner part of each of the sectional slice surfaces in the drawing, the ultrasound received beam signal 29 for each ultrasound transmission shown in a solid line is calculated and output in raster scanning order through electronic scanning, and a sectional slice surface is calculated and output in a certain cycle in the elevation direction. As a result, echo signals in specific positions a, b and c corresponding to focal points in the respective sectional slice planes are output every certain cycle. Accordingly, it is sufficient to give a delay to an output in the certain cycle corresponding to an interval between the sectional slice surfaces from the ultrasound received beam signal 29 stored in the memory unit 7, thereby carrying out an addition. A result of the calculation is obtained as the focal point image F0 on the corresponding imaging line FL.

In the first control phase, a set of signals to be input to the second delay-and-sum unit 9 is fixed and the selecting circuit 8 inputs, to the second delay-and-sum unit 9, data corresponding to necessary sectional slice surfaces (in the example described above, SL#(0) to SL#(4)) in the ultrasound received beam signals 29.

Figure 6:
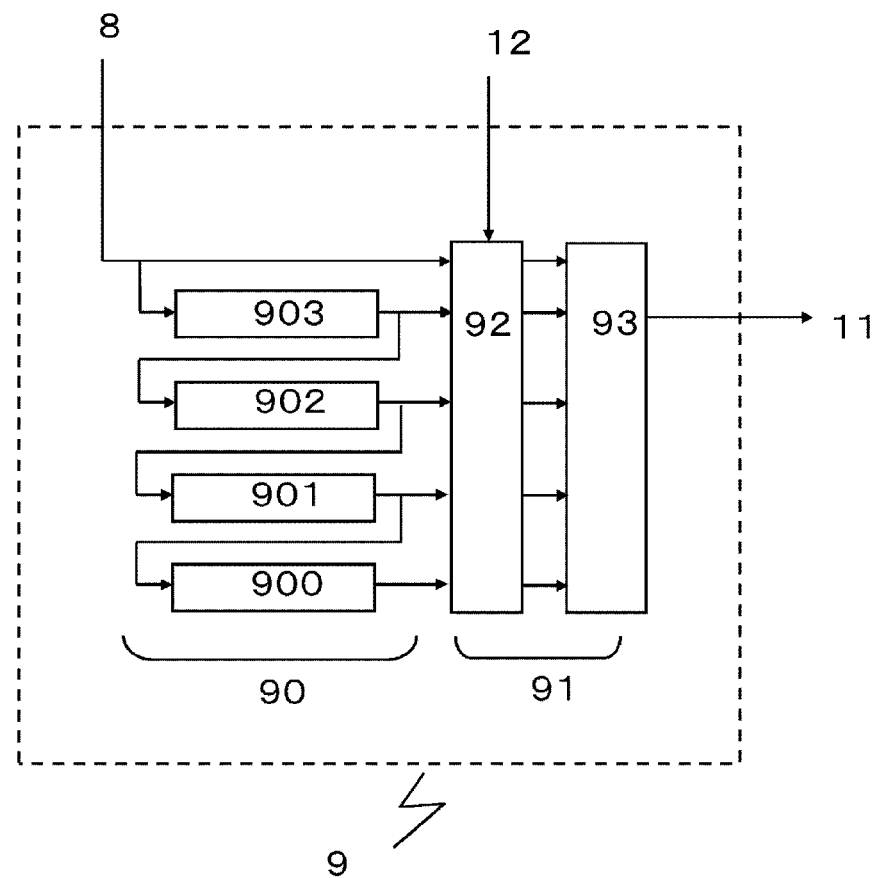
FIG. 6 is a diagram showing an example of a structure of a second delay-and-sum unit according to the present invention.

FIG. 6 shows an example of a preferred structure of the second delay-and-sum unit 9. The second delay-and-sum unit 9 has a slice delay circuit 90 and a delay-and-sum circuit 91. The slice delay circuit 90 is constituted by memories 900 to 903 for storing the ultrasound received beam signals 29 corresponding to a single sectional slice surface respectively. The delay-and-sum circuit 91 is constituted by a delay adjusting circuit 92 and an addition circuit 93. The continuous ultrasound received beam signals 29 selected by the selecting circuit 8 are stored in the memories 900 to 903 of the slice delay circuit 90 in accordance with the sectional slice surface. In the first control phase shown in FIGS. 10A to 10C, the ultrasound received beam signals 29 related to scanning lines on SL#(0) to SL#(4) are stored in the memories 900 to 903 in acquiring order.

When data is sequentially read from the memories 900 to 903, then, echo signals in the same positions of the continuous slice surfaces shown in a, b and c of FIG. 4C can be output in parallel. The delay adjusting circuit 92 selects a delay pattern from the delay pattern set storing memory 11 depending on the time phases in FIGS. 10A to 10C and applies a delay to the ultrasound received beam signal 29 along the scanning line of each sectional slice surface. The addition circuit 93 adds signals sent from the respective sectional slice surfaces. By repeating the processing for each scanning line, it is possible to obtain a result of a delay-and-sum on each imaging line of an imaging plane.

The addition to be carried out by the addition circuit 93 can also include an apodizing processing (an apodization) for applying a weight to each input signal to carry out an addition in the same manner as the addition circuit 28 of the first delay-and-sum unit 6. The apotizing processing has an effect for controlling a receiving aperture or decreasing an influence of an interference wave from a periphery. The weight may be fixed or varied depending on a receiving time to meet a purpose.

In the example, the slice delay circuit is set to be a certain time delay circuit on the assumption that a repetitive pitch of sectional slice surface scanning is constant. In the case in which a pitch is repetitively disordered or a dead time is generated for some reason, however, a unit for properly controlling the start and stop of the slice delay circuit can be additionally provided to always enable an output of echo signals in the same positions of the continuous sectional slice surfaces in parallel. Moreover, both the slice delay circuit 90 and the delay adjusting circuit 92 serve to adjust a delay time. Therefore, they can be unified to form a single delay adjusting circuit or a method of dividing a delay time can be variously changed and executed. However, these modifications are simple design matters, and the gist of the present invention is not changed. In the above description, moreover, the number of the sectional slice surfaces which are to be subjected to the synthetic aperture is set to be five, and the number of the memories 900 to 903 in the slice delay circuit 90 of FIG. 6 is set to be four correspondingly. However, these numbers are only illustrative and a desirable numeric value may be employed.

(Second Control Phase)

Figure 7:
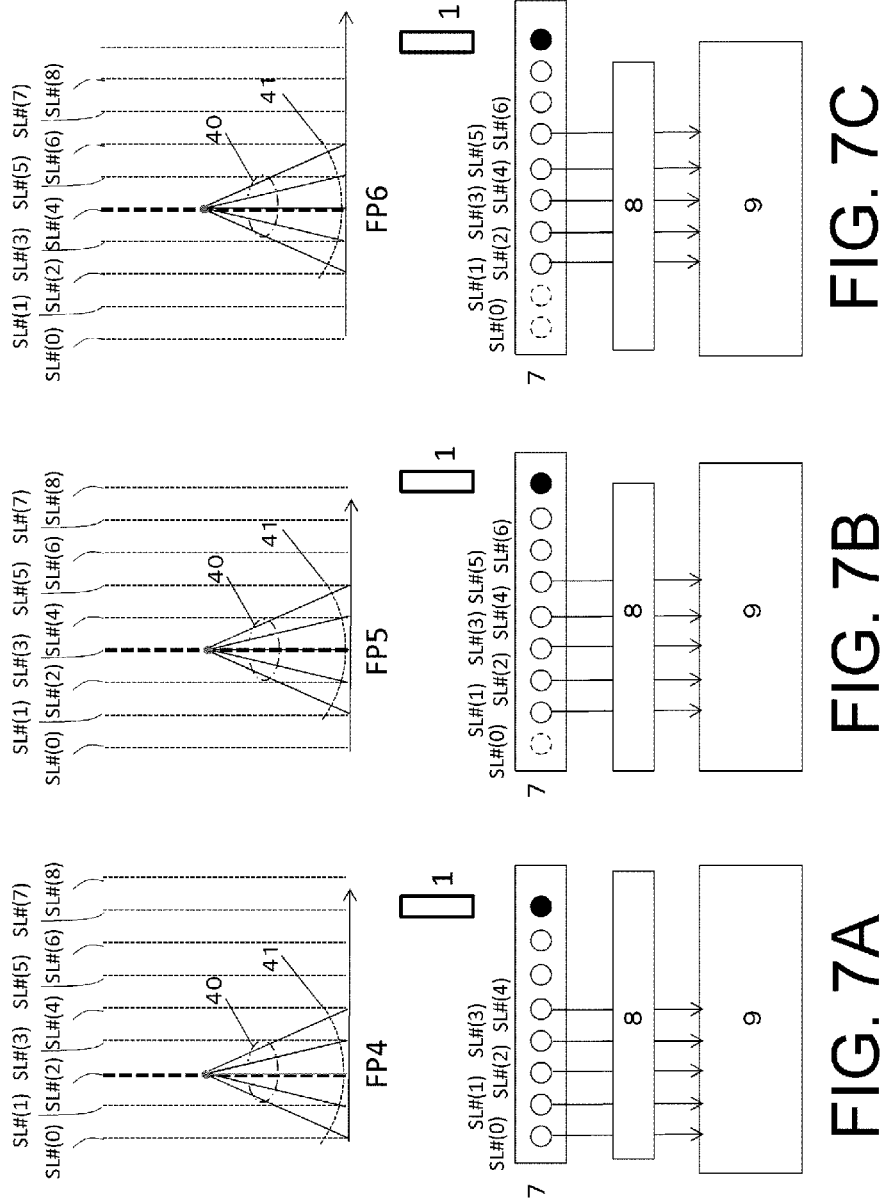
FIGS. 7A to 7C are views for explaining a delay-and-sum in a second control phase according to the present invention.

With reference to FIG. 7, description will be given to a synthetic aperture effect obtained by a delay-and-sum processing to be carried out by the second delay-and-sum unit 9 in the second control phase.

FIGS. 7A to 7C are views showing a state of the first delay-and-sum in the elevation direction in accordance with the mechanical scanning of the probe 1 in the second control phase subsequently to FIGS. 10A to 10C illustrating the first control phase. The second control phase is the same as the method of obtaining an imaging plane through the conventional synthetic aperture processing.

FIG. 7A shows a state in which the probe 1 is moved subsequently to FIG. 10C and an imaging plane FP4 is set correspondingly. The ultrasound received beam signals 29 on the sectional slice surface which are acquired by the electronic scanning of the probe 1 are stored in the memory unit 7. The second delay-and-sum unit 9 inputs the ultrasound received beam signals 29 corresponding to the scanning line signals on the sectional slice surfaces SL#(0) to SL#(4) selected by the selecting circuit 8. At this time, the imaging plane FP4 is set into a position on a middle one of the sectional slice surfaces SL#(0) to SL#(4), and the delay pattern of the second delay-and-sum unit 9 is set in such a manner that an image of a section on an almost center of the aperture in the elevation direction is picked up.

In the second control phase, a delay pattern for the delay-and-sum in the elevation direction which is to be carried out by the second delay-and-sum unit 9 is read from the delay pattern set storing memory 11 and is thus set at a start of the phase. The second delay-and-sum unit 9 carries out the delay-and-sum in the elevation direction by using the delay pattern, thereby obtaining a result of the delay-and-sum on each imaging line over the imaging plane FP4. The result thus obtained is converted into an image signal by the image signaling unit 12 and the image signal is stored, in the image memory 13, as sectional slice image data subjected to the synthetic aperture for the imaging plane FP4.

Also when the probe 1 is moved to obtain the time phase in FIG. 7B, the ultrasound received beam signals 29 on the sectional slice surface acquired by the electronic scanning of the probe 1 are stored in the memory unit 7 in the same manner. At this time, the signal to be input to the second delay-and-sum circuit 9 (the ultrasound received beam signal) is selected again by the selecting circuit 8 through the control of the control unit 10. In other words, specific ones of the ultrasound received beam signals 29 stored in the memory unit 7 are selected by the selecting circuit 8 and are input to the second delay-and-sum unit 9. In the case of FIG. 7B, there are selected the ultrasound received beam signals 29 corresponding to the scanning line signals on the sectional slice surfaces SL#(1) to SL#(5).

In accordance with the example of the structure in FIG. 6, the continuous ultrasound received beam signals 29 selected by the selecting circuit 8 are stored in the memories 900 to 903 of the slice delay circuit 90 in order of the sectional slice surfaces SL#(1) to SL#(5). Data is sequentially read from the memories 900 to 903 and a predetermined delay pattern is given by the slice delay circuit 90 and the delay adjusting circuit 92 so that a result of the delay-and-sum corresponding onto each imaging line over the imaging plane FP5 is obtained. The result is converted into an image signal by the image signaling unit 12 and the image signal is stored, in the image memory 13, as sectional slice image data subjected to the synthetic aperture for the imaging plane FP5.

Also in FIG. 7C showing a state in which the probe 1 is further moved, similarly, sectional slice image data for a imaging plane FP6 is stored in the image memory 13. By continuously carrying out the processing, it is possible to apply an identical delay pattern set first to a delay-and-sum between different sectional slice surfaces, thereby carrying out the synthetic aperture. The sectional slice image data obtained by the synthetic aperture processing is sequentially stored in the image memory 13. By using the identical delay pattern, it is possible to obtain the same shape in the elevation direction of the received beam pattern which is to be subjected to the synthetic aperture. By shifting the sectional slice surfaces of the ultrasound received beam signals 29 to be input to the second delay-and-sum, moreover, it is possible to obtain a synthetic aperture image scanned in the elevation direction.

In the present example, the imaging planes FP4 to FP6 are provided at regular intervals, and there is employed the structure in which they are coincident with the sectional slice surfaces SL#(2) to SL#(4), respectively. By the employment of the structure, the mechanical scanning of the probe 1 and the imaging plane of the sectional image of the synthetic aperture to be created are coincident with each other, and the control to be carried out by the control unit 10 or the image reconstruction to be performed by the image processing unit 14 can be simplified. However, the position of the imaging plane is not restricted to the structure. The position of the imaging plane can also be placed between the sectional slice surfaces. In the case in which the second delay-and-sum is carried out by using the even-numbered sectional slice surfaces, particularly, it is preferable to place the imaging plane in the middle position of the sectional slice surface which is subjected to the delay-and-sum.

Moreover, the position of the imaging plane FP4 at the start of the second control phase is caused to be coincident with the sectional slice surface SL#(2) to be a position on a middle one of the sectional slice surfaces SL#(0) to SL#(4) which are to be subjected to the synthetic aperture. As a result, a symmetry in the elevation direction of the received beam pattern which is to be subjected to the synthetic aperture is enhanced. Consequently, a uniformity in the elevation direction of an image which is to be subjected to the synthetic aperture is increased. If there is employed a structure in which a delay pattern for a second delay-and-sum to be used in the second control phase is held to be constant, however, the positional relationship between the imaging plane and the sectional slice surfaces which are to be subjected to the synthetic aperture is not restricted thereto.

(Third Control Phase)

The second control phase progresses and the processing proceeds to the third control phase when the mechanical scanning of the probe 1 reaches a scanning end point. The ultrasound received beam signals 29 corresponding to the sectional slice surfaces are fixed as signals to be input to the second delay-and-sum unit 9. Then, a delay pattern to be selected from the delay pattern set storing memory 11 is changed, and at the same time, image data are acquired with the movement of the imaging plane which is to be subjected to the synthetic aperture. When an acquired region reaches a predetermined region for an object, all of the processings are ended. In the process, the process for the first control phase described with reference to FIGS. 10A to 10C is carried out in a reverse direction to the elevation probe advancing direction.

However, the movement of the probe 1 may be ended when an imaging scanning end point is reached. By ending the movement of the probe in the mechanical scanning of the probe simultaneously with the termination of the second control phase and then carrying out only the second delay-and-sum processing, it is possible to continuously perform the third control phase. In other words, the ultrasound received beam signals 29 stored in the memory unit 7 are used to change a delay pattern to be selected from the delay pattern set storing memory 11, and at the same time, the imaging plane which is to be subjected to the synthetic aperture is moved to create elevation synthetic aperture data on the imaging plane which is moved. At this time, it is not necessary to carry out electronic scanning for transmitting/receiving an ultrasound wave, thereby creating a new ultrasound received beam signal 29 through the first delay-and-sum unit 6 to store the new ultrasound received beam signal 29 in the memory unit 7. An output subjected to the delay-and-sum with a change in the delay pattern through the second delay-and-sum unit 9 in order to carry out a movement over the imaging plane which is to be subjected to the synthetic aperture is converted into an image signal through the image signaling unit 12, and the image signal is stored, in an image memory, as sectional slice image data of a corresponding imaging plane. It is preferable to end the processing when the sectional slice image data before a predetermined imaging plane is created.

In the present example, the number of the ultrasound received beam signals 29 to be stored in the memory unit 7 is required to be larger, by the number of the surfaces (in the above description, three surfaces) for the execution of the imaging plane movement in the first and third control phases than the number of the sectional slice surfaces to be used for the synthetic aperture (in the above description, M=5). The reason is that the ultrasound received beam signal 29 is to be acquired and stored with the mechanical scanning previously, and at the same time, the synthetic aperture delay-and-sum in the elevation direction is to be carried out by the second delay-and-sum unit 9. For the ultrasound received beam signal 29 to be stored, the number of the sectional slice surfaces to be used in the synthetic aperture (in the above description, M=5) and the number of the imaging planes over which a movement is carried out in the first control phase and the third control phase are enough. By employing a structure for carrying out overwrite to the region of the memory which is not required, therefore, it is possible to efficiently use the memory region.

(Effect of the Example)

In the present example, the ultrasound received beam signal 29 is previously acquired from the probe 1 to carry out the mechanical scanning and is thus stored, and the imaging plane in a delayed position in the mechanical scanning direction from the position of the probe 1 is sequentially subjected to the synthetic aperture in the elevation direction. In other words, a scanning line of the rear imaging plane from the sectional slice surface acquired by the electronic scanning in the position of the probe 1 is subjected to the synthetic aperture by the second delay-and-sum unit 9 and is thus output. With such a structure, the control of the processing for the second delay-and-sum unit 9 is carried out in the division into the first, second and third control phases. Consequently, the movement of the mechanical scanning of the probe 1 becomes uniform for all of the mechanical scanning regions. Therefore, the control for the mechanical control of the probe 1 is simple, and particularly, is suitable for uniformly executing the probe movement in continuous scanning. Consequently, the control for the movement of the probe which is to be carried out by the probe scanning mechanism 2 is simple and easy, and it is possible to produce an advantage that the structure of the apparatus can be complicated and the structure excluding a waste of a mechanical scanning time can be obtained. Furthermore, it is possible to carry out a wide range of imaging in which an imaging region is enlarged to the outside of the mechanical scanning range as shown in FP1 of FIG. 10A.

In the case of the present example, as shown in FIG. 4, the imaging plane is set into the position of the middle one of the sectional slice surfaces in the second control phase. Therefore, the dead zone is generated in the start and end positions of the mechanical scanning of the probe. Accordingly, the first control phase is carried out before the second control phase, and the third control phase is carried out after the second control phase. However, the present invention is not restricted to the example described above. It is preferable to carry out the first control phase or the third control phase depending on the position in which the dead zone is generated.

Example 2

Example 2 employs a suitable structure for the case in which the mechanical scanning of the probe 1 is performed by the step and repeat method. In the present example, the first to third control phases to be carried out by the control unit 10 include the stop or start of the movement of the probe in the mechanical scanning of the probe 1.

Figure 8:
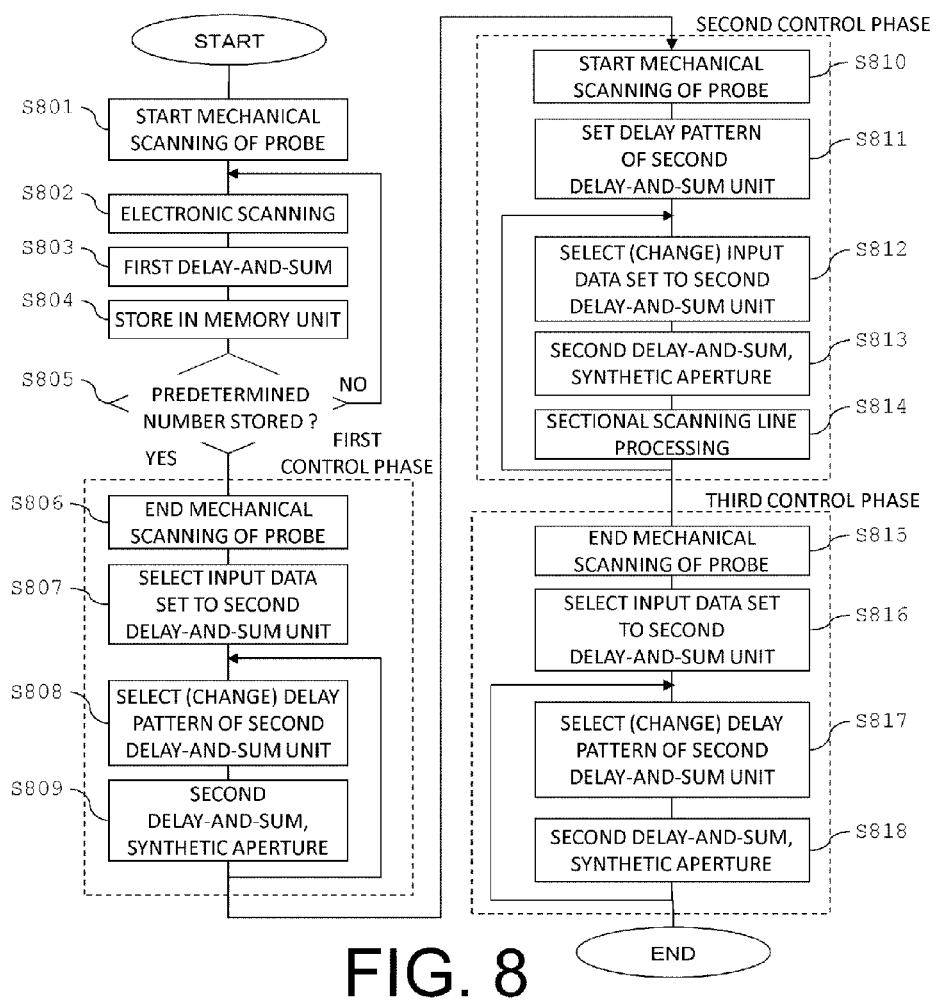
FIG. 8 is a flow chart for explaining a control according to Example 2 of the present invention.

FIG. 8 is a flow chart showing a control processing according to the present example. With regard to a structure of an apparatus and the details of a processing which are common to Example 1, description will be omitted.

At Steps S801 to S805, the same processing as Example 1 is carried out. More specifically, the electronic scanning is carried out with the movement of the probe 1 until a predetermined number M of sectional slice surfaces for performing a synthetic aperture in an elevation direction are acquired. Thus, the ultrasound received beam signal 29 is acquired. The ultrasound received beam signals 29 thus acquired are stored in the memory unit 7. When the ultrasound received beam signals 29 stored in the memory unit 7 correspond to the scanning lines of the predetermined number M of sectional slice surface, the processing proceeds to the first control phase. At this time, the ultrasound received beam signals 29 on the predetermined number M of sectional slice surfaces for carrying out the synthetic aperture in the elevation direction are stored in the memory unit 7.

(First Control Phase)

At Step S806, the movement of the probe 1 is stopped in the probe scanning mechanism 2. In the first control phase according to the present example, the position of the probe 1 is fixed and the electronic scanning through an ultrasound transmission/receipt by the probe 1 is not carried out, and the ultrasound received beam signal 29 stored in the memory unit 7 is used to carry out the same processing as that of the first control phase according to Example 1. However, the movement of the probe 1 and the sectional scanning line processing are not executed.

At Step S807, a set of data to be input to the second delay-and-sum unit is selected from the ultrasound received beam signals 29 stored in the memory unit 7. At Step S808, a delay pattern is selected from the delay pattern set storing memory 11. At Step S809, then, the second delay-and-sum unit 9 carries out the delay-and-sum in the elevation direction (the synthetic aperture processing). A result of the delay-and-sum is output to the image signaling unit 12. Data on the imaging plane which is subjected to image signaling by the image signaling unit 12 is stored in the image memory 13. Subsequently, there is repeated the execution of the delay-and-sum processing in the second delay-and-sum unit 9 by using a delay pattern selected newly from the delay pattern set storing memory 11. The delay patterns stored in the delay pattern set storing memory 11 are caused to correspond to the imaging planes FP1 to FP3 in the same manner as shown in FIGS. 10A to 10C. Consequently, a signal obtained by changing the scanning line constituting the imaging planes FP1 to FP3 into an image is stored in the image memory 13. Every time the imaging plane is moved, the delay-and-sum processing of the second delay-and-sum unit 9 is repeated. In a stage in which a processing for a predetermined imaging plane is ended, the processing proceeds to the second control phase.

(Second Control Phase)

At Step S810, the movement of the probe 1 is started by the probe scanning mechanism 2 again. With the movement of the probe 1, moreover, the sectional scanning line processing is carried out, that is, an ultrasound wave is transmitted/received and electronic scanning is carried out by the probe 1 to create the ultrasound received beam signals 29 and to then store them in the memory unit 7. In the present example, a data size of the ultrasound received beam signal 29 to be stored in the memory unit 7 only corresponds to the predetermined number M of sectional slice surfaces which are to be subjected to the synthetic aperture in the elevation direction. Every time the ultrasound received beam signal 29 of a new sectional slice surface is acquired, it is rewritten in an overwriting form to a memory region which is not required after the synthetic aperture in the memory unit 7.

At Step S811, a delay pattern to be used in the second delay-and-sum unit 9 is selected and set. In the second control phase, the delay pattern is fixed. At Step S812, with the movement of the probe 1 and the sectional scanning line processing, the ultrasound received beam signal 29 updated newly in the memory unit 7 is selected as an input data set. At Step S813, the second delay-and-sum unit 9 carries out a delay-and-sum over the selected data (a synthetic aperture processing) and outputs a result to the image signaling unit 12. Data on the imaging plane subjected to the image signaling through the image signaling unit 12 is stored in the image memory 13. Image scanning line data on the imaging plane corresponding to the movement of the probe 1 is stored in the same manner as FP4 to FP6 shown in FIG. 7 for the imaging plane 13. At Step S814, subsequently, the sectional scanning line processing with the movement of the probe 1 is carried out continuously.

(Third Control Phase)

At Step S815, when the mechanical scanning of the probe 1 reaches a scanning end point, the probe scanning mechanism stops the mechanical scanning of the probe. Processings of subsequent Steps S816 to S818 are the same as the processing of the first control phase, and an imaging plane of a dead zone is created and an imaging plane out of the mechanical scanning range is created depending on the situation.

In the present example, it is sufficient that the ultrasound received beam signals 29 to be stored in the memory unit 7 correspond to the predetermined number M of sectional slice surfaces for carrying out the synthetic aperture in the elevation direction. For this reason, it is not necessary to store the data on the sectional scanning line processing of the probe 1 in the mechanical scanning prior to the processing for each imaging plane as in Example 1. Accordingly, the structure of the memory unit 7 can be reduced more greatly to cut down a cost.

In the case in which the mechanical scanning of the probe 1 is carried out by the step and repeat method, particularly, it is possible to suitably carry out the processing in the second delay-and-sum unit 9 in combination with the control for the probe movement which is to be performed by the control unit 10.

Example 3

In Example 3, controls having different ultrasound transmitting pattern conditions for acquiring an ultrasound echo signal are carried out in the first to third control phases to be performed by the control unit 10. In the present example, furthermore, the transducer array provided on the probe 1 has a 1.5D, 1.75D or 2D structure. By using the transducer arrays, it is possible to control a transmitting beam pattern in the elevation direction. Moreover, the present example has a feature that different controls are carried out in the first to third control phases to be performed through the control unit 10 by using the ultrasound transmitting pattern conditions in order to change the transmitting beam pattern in the elevation direction.

First of all, description will be given to a change in the transmitting pattern in the elevation direction using the probe 1 according to the present example. In the present example, as an almost one-dimensional transducer array, there is used a transducer array in which transducer elements are divided also in the elevation direction and ultrasound transmitting and driving operations can be carried out independently in the elevation direction. For instance, there are transducer arrays having 1.5D, 1.75D and 2D structures. For simplicity, description will be given to the 1.5D array. However, the 1.75D or 2D array may be used.

FIG. 9A is a sectional view showing the 1.5D transducer array in the elevation direction. The transducer array 16 is divided into a plurality of parts (which is set to be five parts) in the elevation direction, and the transducer elements arranged symmetrically around a center are connected and driven in a lump. The elements to be driven at the same time are indicated as the same number, a central element column is indicated as 160, an element column in a first side column is indicated as 161, and an element column in a second side column is indicated as 162. The transmitting unit 4 can independently drive the element columns 160, 161 and 162 through a switching circuit which is not shown, and the connection of the switching circuit can be controlled as the ultrasound transmitting pattern condition by the control unit 10. An acoustic lens for converging an ultrasound wave in the elevation direction may be provided on the 1.5D transducer array transmitting side. In the present invention for carrying out the synthetic aperture in the elevation direction, however, a greater angular aperture of an ultrasound beam is preferable. Therefore, a structure having no acoustic lens is more preferable.

FIGS. 9B to 9D are schematic views showing the angular aperture in the elevation direction in the case in which a condition is changed to drive the transducer array 16 through the connection of the switching circuit. FIG. 9B shows the case in which only the central element column 160 is driven, FIG. 9C shows the case in which the central element column 160 and the element column 161 in the first side column are driven, and FIG. 9D shows the case in which all of the element columns (the central element column 160, the element column 161 in the first side column and the element column 162 in the second side column) are driven.

In the case in which the transducer array 16 is driven by only the central element column 160 shown in FIG. 9B, the angular aperture is great because of a small driving effective element width in the elevation direction and an ultrasound transmission is carried out within a wide range in the elevation direction. On the other hand, a sound pressure density of a transmitted ultrasound wave is reduced. From FIG. 9C to FIG. 9D, gradually, the driving element column is increased so that the driving effective element width in the elevation direction is increased. Moreover, the angular aperture is reduced so that the width of the transmitted ultrasound beam pattern in the elevation direction is decreased.

Thus, the connection of the switching circuit is controlled as the ultrasound transmitting pattern condition by the control unit 10, and the width of the transmitted ultrasound beam pattern in the elevation direction can be controlled by a variation in the driving effective element width.

By generating a time delay between the driving pulses of the central element column 160, the element column 161 in the first side column and the element column 162 in the second side column, furthermore, it is possible to form a transmission beam in the elevation direction. For example, it is possible to create the transmitted ultrasound beam converting in the elevation direction by aligning the phases of the driving pulses in the central element column 160, the element column 161 in the first side column and the element column 162 in the second side column with respect to a set transmission focus.

FIG. 9E is a schematic view showing the transmitted ultrasound beam thus formed. At this time, it is also possible to intentionally reduce the convergence of a transmitted ultrasound beam by slightly shifting the phase of the driving pulse of the element column 162 in the second side column from the phase of the driving pulse in the other element column, for example. FIG. 9F is a schematic view showing the transmitted ultrasound beam thus formed, and the transmitted ultrasound beam pattern in the elevation direction has a greater width than the transmitted ultrasound beam in FIG. 9E. Moreover, FIG. 9G is a schematic view showing the case in which a position of a transmission focus is set to be closer and the phase of the driving pulse of the element column 162 in the second side column is greatly shifted from the phase of the driving pulse in the other element column.

By shifting the driving pulses in the central element column, the first side column and the second side column to give a time difference, thereby carrying out a control by the control unit 10 as the ultrasound transmitting pattern condition, thus, it is possible to control the width of the transmitted ultrasound beam pattern in the elevation direction.

In the present example, the ultrasound transmitting pattern condition of the ultrasound transmission described above is added into control items to be carried out by the control unit 10, and the ultrasound transmitting pattern conditions are changed through the first to third control phases.

In other words, in the first control phase, there is used the ultrasound transmitting pattern condition for increasing the width of the transmitted ultrasound beam pattern in the elevation direction of the ultrasound wave to be transmitted for acquiring the ultrasound received beam signal 29. In the second control phase, moreover, there is used the ultrasound transmitting pattern condition for reducing the width of the transmitted ultrasound beam pattern in the elevation direction of the ultrasound wave to be transmitted for acquiring the ultrasound received beam signal 29. In the third control phase, the same control as that of the first control phase is carried out.

The ultrasound transmitting pattern condition for increasing the width of the transmitted ultrasound beam pattern in the elevation direction may be the connection of the switching circuit shown in FIG. 9B or the time difference between the driving pulses in the central element column, the first side column and the second side column shown in FIG. 9G.

Moreover, the ultrasound transmitting pattern condition for reducing the width of the transmitted ultrasound beam pattern in the elevation direction may be the connection of the switching circuit shown in FIG. 9D or the time difference between the driving pulses in the central element column, the first side column and the second side column shown in FIG. 9E.

When the control is carried out, the width of the transmitted ultrasound beam pattern in the elevation direction is increased in the first control phase. As a result, as in the imaging plane FP1 in FIG. 10A, an ultrasound wave also goes around a wide range of a surface displaced apart from the probe 1 for carrying out the ultrasound transmission so that an ultrasound echo wave can be received by the probe 1.

In the second control phase, moreover, the imaging plane is set onto almost centers of the sectional slice surfaces to be used for a synthetic aperture. In this case, the probe position for acquiring the ultrasound echo and the imaging plane are not provided greatly apart from each other. Therefore, the wraparound of the transmitted ultrasound wave is more excellent than that in the first control phase. In this case, it is possible to prevent a reduction in the sound pressure density of the transmitted ultrasound beam by decreasing the width of the transmitted ultrasound beam pattern in the elevation direction. Thus, it is possible to ensure a general SN ratio of the ultrasound echo wave.

By including the execution of the control having the difference ultrasound transmitting pattern conditions through the first control phase and the second control phase in the control to be carried out by the control unit 10, it is possible to give a condition that the SN ratio of the ultrasound echo wave to the imaging plane is suitable in each of the control phases. Consequently, the second delay-and-sum based on the suitable synthetic aperture principle can be carried out in each probe position following the mechanical scanning.

The present example can also be combined with any of Examples 1 and 2.

In the present example, moreover, the delay condition for giving the driving pulse of each transducer element provided on the transducer array and the number of the driving elements in the elevation direction are used as the ultrasound transmitting pattern conditions. In addition, however, it is also possible to control the transmitting condition capable of controlling the width of the transmitted ultrasound beam pattern in the elevation directions. In particular, it is also possible to give a change to a driving pulse amplitude or a driving pulse width in the elevation direction, thereby carrying out a transmitting apotization for applying a distribution in the elevation direction to a strength of the ultrasound wave to be transmitted from the transducer element. By causing the conditions of the transmitting apotization to be different from each other between in the first control phase and in the second control phase, it is possible to produce the same effect as that in the present example.

In the case in which the 1.75D or 2D array is used, furthermore, the transducers arranged in the elevation direction can be driven asymmetrically. By giving a delay to the driving pulse asymmetrically, therefore, it is also possible to apply a deflection angle in the elevation direction to the transmission beam. By causing these transmitting conditions to be different from each other between in the first control phase and in the second control phase, it is possible to obtain the same effects as those in the present example.

While the present invention has been described with reference to exemplary embodiments, it is to be understood that the invention is not limited to the disclosed exemplary embodiments. The scope of the following claims is to be accorded the broadest interpretation so as to encompass all such modifications and equivalent structures and functions.

This application claims the benefit of Japanese Patent Application No. 2011-026095, filed on Feb. 9, 2011, which is hereby incorporated by reference herein in its entirety.

The invention claimed is:

1. An object information acquiring apparatus comprising:
a probe which is configured to carry out electronic scanning in a first direction in which a plurality of elements each transmitting an ultrasound wave to an object and outputting a receiving signal upon receipt of the reflected ultrasound wave are arranged;
a scanning unit which is configured to carry out mechanical scanning of the probe in a second direction intersecting with the first direction over a parallel plane with a receiving surface of each of the elements;
a first delay-and-sum unit which is configured to carry out a delay-and-sum in the first direction by using the receiving signal, thereby generating a first delay-and-sum signal;
a memory unit which is configured to store the first delay-and-sum signal in each position in the second direction for each sectional plane;
a second delay-and-sum unit which is configured to carry out a delay-and-sum in the second direction by using a predetermined number of first delay-and-sum signals corresponding to M sectional planes (where M is a predetermined integer equal to two or more) from among the first delay-and-sum signals stored in the memory unit, thereby generating a second delay-and-sum signal, the second delay-and-sum signal output from the second delay-and-sum unit being used to acquire information in the object as image data, wherein the second delay-and-sum unit:
(a) is configured to perform the delay-and-sum in a first manner, in which a set of the M sectional planes is fixed and the first delay-and-sum signals relating to the fixed M sectional planes are added while a delay pattern is varied, so as to generate the second delay-and-sum signal, and
(b) is configured to perform the delay-and-sum in a second manner, in which the set of the M sectional planes is varied and the first delay-and-sum signals relating to the M sectional planes are added while the delay pattern is fixed, so as to generate the second delay-and-sum signal.

2. The object information acquiring apparatus according to claim 1, wherein, in a case of the first manner, the delay-and-sum is performed at a starting position of the mechanical scanning of the probe, and and in a case of the second manner, the delay-and-sum is performed after the first manner.

3. The object information acquiring apparatus according to claim 1, wherein, in a case of the first manner, the delay-and-sum is performed at an ending position of the mechanical scanning of the probe, and in a cause of the second manner, the delay-and-sum is performed before the first manner.

4. The object information acquiring apparatus according to claim 1, wherein, in a case of the first manner, the delay-and-sum is performed at a starting position and an ending position of the mechanical scanning of the probe, and in a case of the second manner, the delay-and-sum is performed between the first manner which is performed at the starting position and the ending position.

5. The object information acquiring apparatus according to claim 1, wherein the probe has a plurality of elements arranged also in the second direction, and elements to be driven are controlled to form ultrasound transmission beams having different shapes between in the first case and in the second case.

6. The object information acquiring apparatus according to claim 1, wherein three-dimensional image data is generated by using the second delay-and-sum signal.

7. An object information acquiring comprising:
a probe which is configured to carry out electronic scanning in a first direction in which a plurality of elements each transmitting an ultrasound wave to an object and outputting a receiving signal upon receipt of the reflected ultrasound wave are arranged;
a scanning unit which is configured to carry out mechanical scanning of the probe in a second direction intersecting with the first direction over a parallel plane with a receiving surface of each of the elements;
a first delay-and-sum unit which is configured to carry out a delay-and-sum in the first direction by using the receiving signal, thereby generating a first delay-and-sum signal;
a memory unit which is configured to store the first delay-and-sum signal in each position in the second direction for each sectional plane; and
a second delay-and-sum unit which is configured to carry out a delay-and-sum in the second direction by using a predetermined number of first delay-and-sum signals corresponding to M sectional planes (where M is a predetermined integer equal to two or more) from among the first delay-and-sum signals stored in the memory unit, thereby generating a second delay-and-sum signal, the second delay-and-sum signal output from the second delay- and-sum unit being used to acquire information in the object as image data,
wherein the second delay-and-sum unit is configured to perform the delay-and- sum in a first manner, in which a set of the M sectional planes is fixed and the first delay-and- sum signals relating to the fixed M sectional planes are added while a delay pattern is varied, so as to generate the second delay-and-sum signal.

8. The object information acquiring apparatus according to claim 7, wherein three-dimensional image data is generated by using the second delay-and-sum signal.

* * * * *